US007244830B2

(12) United States Patent
Chaikof et al.

(10) Patent No.: US 7,244,830 B2
(45) Date of Patent: Jul. 17, 2007

(54) GLYCOPOLYMERS AND FREE RADICAL POLYMERIZATION METHODS

(75) Inventors: Elliot L. Chaikof, Atlanta, GA (US); Daniel Grande, Vitry-sur-Sein (FR); Subramanian Baskaran, Foster City, CA (US)

(73) Assignee: Emory University, Atlanta, GA (US)

( * ) Notice: Subject to any disclaimer, the term of this patent is extended or adjusted under 35 U.S.C. 154(b) by 72 days.

(21) Appl. No.: 10/451,011

(22) PCT Filed: Jan. 14, 2002

(86) PCT No.: PCT/US02/01030

§ 371 (c)(1),
(2), (4) Date: Nov. 24, 2003

(87) PCT Pub. No.: WO02/055021

PCT Pub. Date: Jul. 18, 2002

(65) Prior Publication Data

US 2004/0116677 A1    Jun. 17, 2004

Related U.S. Application Data

(60) Provisional application No. 60/261,275, filed on Jan. 12, 2001.

(51) Int. Cl.
*C07H 5/06* (2006.01)
*C07H 1/00* (2006.01)
(52) U.S. Cl. .................. 536/18.7; 536/55.2; 536/122; 536/123.1; 536/123.13; 536/124
(58) Field of Classification Search .............. 536/18.7, 536/55.2, 122, 123.1, 123.13, 124
See application file for complete search history.

(56) References Cited

U.S. PATENT DOCUMENTS 4,485,045 A    11/1984    Regen ..................... 260/403
4,522,803 A    6/1985    Lenk et al. ............... 424/1.1

(Continued)

FOREIGN PATENT DOCUMENTS

WO    WO 96/21469    7/1996

(Continued)

OTHER PUBLICATIONS

Akagawa, M. and Suyama, K., "Mechanism of formation of elastin crosslinks," (2000) *Connect. Tissue Res.* 41(2):131-141.

(Continued)

*Primary Examiner*—Shaojia Anna Jiang
*Assistant Examiner*—Everett White
(74) *Attorney, Agent, or Firm*—Greenlee, Winner and Sullivan, P.C.

(57) ABSTRACT

A glycopolymer composition is provided comprising glycopolymer molecules having a polymer backbone; a first pendent unit comprising a linking group connected to said polymer backbone and a saccharide moiety connected to said linking group, optionally a second pendent unit; a phenyl ring at a first end of the polymer backbone; and a cyanoxyl group at the second end of the polymer backbone, useful as intermediates for making bioactive glycopolymers which bind to bioactive molecules, viruses, cells and substrates for protein separation, cell culture, ad drug delivery systems, as well as in targeting for treatment of wound healing and other pathological conditions.

33 Claims, 3 Drawing Sheets

U.S. PATENT DOCUMENTS

| | | | |
|---|---|---|---|
| 4,560,599 A | 12/1985 | Regen | 428/36 |
| 4,880,883 A | 11/1989 | Grasel et al. | 535/454 |
| 4,906,465 A | 3/1990 | Chaikof et al. | 424/78 |
| 5,071,532 A | 12/1991 | Taillet et al. | 204/228 |
| 5,288,517 A | 2/1994 | Kanno et al. | 427/244 |
| 5,399,331 A | 3/1995 | Loughrey et al. | 424/450 |
| 5,417,969 A | 5/1995 | Hsu et al. | 424/78 |
| 5,429,618 A | 7/1995 | Keogh | 604/266 |
| 5,741,325 A | 4/1998 | Chaikof et al. | 623/1 |
| 5,755,788 A | 5/1998 | Strauss | 623/11 |
| 5,911,942 A | 6/1999 | Fofonoff et al. | 264/444 |
| 6,071,532 A | 6/2000 | Chaikof et al. | 424/450 |
| 6,171,614 B1 | 1/2001 | Chaikof et al. | 424/450 |
| 6,583,251 B1 | 6/2003 | Chaikof et al. | 526/277 |

FOREIGN PATENT DOCUMENTS

| | | |
|---|---|---|
| WO | WO 98/16198 | 4/1998 |
| WO | WO 00/00239 | 1/2000 |
| WO | WO 01/78800 | 4/2001 |
| WO | WO 01/80921 | 4/2001 |
| WO | WO 02/09647 | 7/2001 |
| WO | WO 02/055021 | 1/2002 |

OTHER PUBLICATIONS

Akita, K. et al., Effect of FK506 and anti-CD4 therapy on fetal pig pancreas xenografts and host lymphoid cells in NOD/Lt, CBA, and BALB/c mice, (1994) *Cell Transplantation* 3(1):61-73.

Anderson et al., "Bioactive silk-like protein polymer films on silicon devices," Alper, M., Bayby, H., Kaplan, D. and Navia, M., ed.; *Materials Research Society Symp Proc.*: Pittsburgh, PA; 1994, 330:171-177.

Andree, H.A.M. et al., "Transport rate limited catalysis on macroscopic surfaces: the activation of factor X in a continuous flow enzyme reactor," (1994) *Biochemistry* 33(14):4368-4374.

Aoi, K. et al., "Glycopeptide synthesis by an α-amino acid N-carboxyanhydride (NCA) method: ring-opening polymerization of a sugar-substituted NCA," (1994) *Macromolecules* 27:875-877.

Aoi, K. et al., "Architectural control of sugar-containing polymers by living polymerization: ring-opening polymerization of 2-oxazolines initiated with carbohydrate derivatives," (1992) *Macromolecules* 25:7073-7075.

Arnander, C. and Olsson, P., "Influence of blood flow and the effect of protamine on the thromboresistant properties of a covalently bonded heparin surface," (1988) *J. Biomed. Mater. Res.* 22(10):859-868.

Balachander, N. and Sukenik, C.N., "Monolayer transformation by nucleophilic substitution: applications to the creation of new monolayer assemblies," (1990) *Langmuir* 6(11):1621-1627.

Basmadjian, D. et al., "Coagulation on biomaterials in flowing blood: some theoretical considerations," (1997) *Biomaterials* 17(23):1511-1522.

Basmadjian, D. and Sefton, M.V., "Relationship between release rate and surface concentration for heparinized materials," (1983) *Journal of Biomedical Materials Research* 17(3):509-518.

Beyer, D. et al., "Covalently attached polymer mono- and multilayers on silanized glass substrates," (1996) *Thin Solid Films* 285:825-828.

Bierbaum, K. et al., "A near edge X-ray absorption fine structure spectroscopy and X-ray photoelectron spectroscopy study of the film properties of self-assembled monolayers of organosilanes on oxidized Si(100)," (1995) *Langmuir* 11:512-518.

Biessen, E.A.L. et al., "Synthesis of cluster galactosides with high affinity for the hepatic asialoglycoprotein receptor," (1995) *J. Med. Chem.* 38:1538-1546.

Billy, D. et al., "Prothrombin activation by prothrombinase in a tubular flow reactor," (1995) *J. Biol. Chem.* 270(3):1029-1034.

Biro, S. et al., "Expression and subcellular distribution of basic fibroblast growth factor are regulated during migration of endothelial cells," (1994) *Circ. Res.* 74:485-494.

Bitomsky, W. and Wade, R.C., "Docking of glycosaminoglycans to heparin-binding proteins: validation for aFGF, bFGF, and antithrombin and application to IL-8," (1999) *J. Am. Chem. Soc.* 121:3004-3103.

Björquist, P. et al., "Determination of the inetic constants of tissue factor/factor VII/factor VIIA and antithrombin/heparin using surface plasmon resonance," (1997) *Thromb. Res.* 85(3):225-236.

Blezer, R. et al., "Initiation and propagation of blood coagulation at artificial surfaces studied in a capillary flow reactor," (1998) *Thromb. Haemostasis* 79(2):296-301.

Blezer, R. et al., "Activation of blood coagulation at heparin-coated surfaces," (1997) *J. Biomedical Materials Research* 37(1):108-113.

Bon, S.A.F. and Haddleton, D.M., "Amphiphilic copolymers by atom transfer polymerization with carbohydrate-based initiators and monomers," (1999) *Polym. Prepr.* (Am. Chem. Soc., Div. Polym. Chem.) 40(2):248-249.

Bourin, M.C. and Lindahl, U., "Glycosaminoglycans and the regulation of blood coagulation," (1993) *Biochemical J.* 289(Pt2):313-330.

Brittain, H.A. et al., "Sickle erythrocyte adherence to large vessel and microvascular endothelium under physiologic flow is qualitatively different," (1992) *J. Lab. Clin. Med.* 112:538-545.

Broch, H. et al., "Quantum molecular modeling of the elastinic tetrapeptide Val-Pro-Gly-Gly," (1998) *J. Biomol. Struct. & Dyn.* 15:1073-1091.

Brown, D.F.M., "Treatment options for deep venous thrombosis," (Nov. 2001) *Emergency Medicine Clinics of North America* 19(4):913-923.

Brummel, .E. et al., "An integrated study of fibrinogen during blood coagulation," (1999) *J. Biol. Chem.* 274(32):22862-22870.

Buller, C.E. et al., "Primary stenting versus balloon angioplasty in occluded coronary arteries," (1999) *Circulation* 100(3):236-242.

Byun, Y. et al., "Binding of antithrombin III and thrombin to immobilized heparin under flow conditions," (1996) *Biotechnology Progress* 12(2):217-225.

Byun, Y. et al., "Mechanism of thrombin inactivation by immobilized heparin," (1996) *J. Biomed. Mater. Res.* 30:423-427.

Cai, W.Z. et al., "A solid-state n.m.r. study of microphase structure and segmental dynamics of poly(styrene-b-methylphenylsiloxane) diblock copolymers," (1993) *Polymer* 34:267-276.

Campbell, E.J. et al., "Biocompatible surfaces using methacryloylphosphorylcholine laurylmethacrylate copolymer," (1994) *ASAIO J.* 40(3):M853-M857.

Calistri-Yeh, M. et al., "Thermal stability of self-assembled monolayers from alkylchlorosilanes," (1996) *Langmuir* 12:2747.

Cao, Q. et al., "Sequence of abductin, the molluscan 'rubber' protein," (1997) *Curr. Biol.* 7:R677-678.

Chaikof, E.L., "Biomaterials that imitate cell microenvironments," (1996) *Chemtech.* 26:17-24.

Chaikof, E.L. et al., "PEO enhancement of platelet deposition, fibrinogen deposition, and complement C3 activation," (1992) *J. Biomed. Mater. Res.* 26:1163-1168.

Chang, D.K. et al., "Nuclear overhauser effect and computational characterization of the β-spiral of the polypentapeptide of elastin," (1989) *J. Biomol. Struct. Dyn.* 6(5):851-858.

Chang, D.K. and Urry, D.W., "Molecular dynamics calculations on relaxed and extended states of the polypentapeptide of elastin," (1988) *Chem. Phys. Lett.* 147:395-400.

Chapman, D., "Biomembranes and new hemocompatible materials," (1993) *Langmuir* 9:39-45.

Chen, C. et al., "Phosphorylcholine coating of ePTFE grafts reduces neointimal hyperplasia in canine model," (1997) *Ann. Vasc. Surg.* 11(1):74-79.

Chen, T-M et al., "Studies on the synthesis and properties of novel phospholipid analogous polymers," (1996) *J. Appl. Polym. Sci.* 60:455-464.

Cheung, J. H. et al., "Molecular self-assembly of conducting polymers," (1994) *Thin Solid Films* 244:985-989.

Chon, J.H. et al., "Cytomimetic biomaterials. 3. Preparation and transport studies of an alginate/amphiphilic copolymer/polymerized phospholipid film," (1999) *J. Biomater. Sci. Polymer. Ed.* 10:95-107.

Chon, J.H. et al., "α4β1 and α5β1 control cell migration on fibronectin by differentially regulating cell speed and motile cell phenotype," (1998) Ann. Biomed. Eng. 26:1091-1101.

Chon, J.H. et al., "Role of fibronectin and sulfated proteoglycans in endothelial cell migration on a cultured smooth muscle layer," (1997) J. Surg. Res. 72:53-59.

Christianson, S. et al., "Adoptive transfer of diabetes into immunodeficient NOD-scid/scid mice: relative contributions of CD4+ and CD8+ T-cells from diabetic versus prediabetic NOD. NON-Thy-1ª donors," (1993) Diabetes 42:44-55.

Cima, L.G. and Lopina, S.T., "Network structures of radiation-cross-linked star polymer gels," (1995) Macromolecules 28:6787-6794.

Clowes, AW et al., "Mechanisms of arterial graft failure. II. Chronic endothelial and smooth muscle cell proliferation in healing polytetrafluoroethylene prostheses," (1986) J. Vasc. Surg. 3:877-884.

Clowes, A.W. et al., "Mechanism of arterial graft failure. 1. Role of cellular proliferation in early healing of PTFE prostheses," (1985)Am. J. Pathol. 118(1:43-54.

Clowes, A.W. and Karnovsky, M.J., "Suppression by heparin of smooth muscle cell proliferation in injured arteries," (1977) Nature 625-626.

Colton, C.K., "The engineering of xenogeneic islet transplantation by immunoisolation," (1992) Diab. Nutr. Metabol. 5:145-149.

Colton, C. and Avgoustiniatos, E. "Bioengineering in the development of the hybrid artificial pancreas I" (1991) Biochem. Eng. 113:152-70.

Contino, P.B. et al., "Use of an oriented transmembrane protein to probe the assembly of a supported phospholipid bilayer," (1994) Biophys. J. 67:1113-1116.

Crooks, C.A., et al., "Microencapsulation of mammalian cells in a HEMA-MMA copolymer: effects on capsule morphology and permeability,"(1990) J. Biomed. Mater. Res. 24: 1241-1262.

Cruise, G.M. et al., "A sensitivity study of the key parameters in the interfacial photopolymerization of poly(ethylene glycol) diacrylate upon porcine islets," (1998) Biotechnol. Bioeng. 57: 655-65.

Daugherty, D. L. and Gellman, S. H., "A fluorescence assay for leucine zipper dimerization: avoiding unintended consequences of fluorophore attachment," (1999) J. Am. Chem. Soc. 121:4325-4333.

Dautzenberg, H. et al., Polyelectrolyte complex formation at the interface of solutions, (1996), Polym. Sci. 101:149-156.

Debelle, L. and Tamburro, A.M., "Elastin: molecular description and function," (1999) Internat. J. Biochem. & Cell Biol. 31:261-272.

Decher, G., "Fuzzy nanoassemblies: toward layered polymeric multicomposites," (1997) Science 277:1232-1237.

Defrees, S.A. et al., "Sialyl lewis x liposomes as a multivalent ligand and inhibitor of E-selectin mediated cellular adhesion," (1996) J. Am. Chem. Soc. 118:6101-6104.

Deming, T. J., "Mussel byssus and biomolecular materials," (1999) Curr. Opin. Chem. Biol. 3: 100-5.

Dixon, W. T., "Spinning-sideband-free and spinning-sideband-only NMR spectra in spinning samples," (1982) J. Chem. Phys. 77:1800-1809.

Dixon, W.T., "Total suppression of sidebands in CPMAS C-13 NMR," (1982) J. Magn. Reson. 49:341-345.

Dluhy, R.A., "Quantitative external reflection infrared spectroscopic analysis of insoluble monolayers spread at the air-water interface," (1986) J. Phys. Chem. 90:1373-1379.

Dodson, G.G. et al., "molecular recognition in insulin assembly," (1993) Biochem. Soc. Trans. 21:609-614.

Doshi, J. and Reneker, D.H., "Electrospinning process and applications of electrospun fibers," (1995) J. Electrostatics 35: 151-160.

Eaton, D. F., "Dye sensitized photo polymerization," (1986) Advances in Photochemistry 13:427-487.

Egger, N. et al., "Solid state NM investigation of cationic polymerized epoxy resins," (1992) J. Appl. Poly. Sci. 44:289-295.

Einaga, Y. et al., "Photofunctional vesicles containing Prussian blue and azobenzene," (1999) J. Am. Chem. Soc. 121:3745-3750.

Eitzman, D.T. et al., "Heparin neutralization by platelet-rich thrombi," (1994) Circulation 89(4):1523-1529.

Elbert, D. L. et al., "Thin polymer layers formed by polyelectrolyte multilayer techniques on biological surfaces," (1999) Langmuir 15:5355-5362.

Elender, G. et al., "Functionalisation of Si/SiO$_2$ and glass surfaces with ultrathin dextran films and deposition of lipid bilayers," (1996) E. Biosensors Bioelectronics 11:565-577.

Elliott, J. T. and Prestwich, G. D., "Maleimide-functionalized lipids that anchor polypeptides to lipid bilayers and membranes," (2000) Bioconjugate Chem. 11:832-841.

Esmon, C.T. et al., "Regulation and functions of the protein C anticoagulant pathway," (1999) Haematologica 84(4):363-368.

Esmon, C.T. et al., "The protein C pathway: new insights," (1997) Thromb. Haemostasis 78(1):70-74.

Esmon, C.T., "Thrombomodulin as a model of molecular mechanisms that modulate protease specificity and function at the vessel surface," (1995) FASEB Journal 9(10):946-955.

Esmon, C.T. and Owen, W.G., "Identification of an endothelial cell cofactor for thrombin-catalyzed activation of protein C," (1981) Proc. Natl. Acad. Sci. USA 78(4):2249-2252.

Esmon, N.L. et al., "Proteolytic formation and properties of y-carboxyglutamic acid-domainless protein C," (1983) J. Biol. Chem. 258(9):5548-5553.

Esmon, N.L. et al., "Thrombomodulin blocks the ability of thrombin to activate platelets," (1983) J. Biol. Chem. 258(20):12238-12242.

Esmon, N.L. et al., "Isolation of a membrane-bound cofactor for thrombin-catalyzed activation of protein C," (1982) J. Biol. Chem. 257(2):859-864.

España, F. et al., "In vivo and in vitro complexes of activated protein C with two inhibitors in baboons," (1991) Blood 77(8):1754-1760.

Faham, S. et al. "Heparin structure and interactions with basic fibroblast growth factor," (1996) Science 271:1116-1120.

Feingold, H.M. et al., "Coagulation assays and platelet aggregation patterns in human, baboon, and canine blood," (1986) Am. J. Vet. Res. 47:2197-2199.

Feng, J. and Chaikof, E.L., "Reconstitution of thrombomodulin into polymerizable phospholipid vesicles," (2000) Polymer Preprints 41(2):1653-1654.

Flitsch, S.L., "Chemical and enzymatic synthesis of glycopolymers," (Dec. 2000) Current Opinion in Chem. Biol. 4(6):619-625.

Florin, E.L. and Gaub, H.E., "Painted supported lipid membranes," (1993) Biophys J. 64:375-383.

Fong, H. et al., "Beaded nanofibers formed during electrospinning," (1999) Polymer 40: 4585-4592.

Foster, J.A. et al., "Isolation and amino acid sequences of tropoelastin peptides," (1973) J. Biol. Chem. 24:2876-2879.

Franzblau, C. et al., "Role of crosslinking in fiber formation," (1977) Adv. Exp. Med. Biol. 79:313-327.

Galvin, J.B. et al., "Reconstitution of rabbit thrombomodulin into phospholipid vesicles," (1987) J. Biol. Chem. 262(5):2199-2205.

Gemmell, C.H. et al., "The effects of shear rate on the enzymatic activity of the tissue factor-factor VIIa complex," (1990) Microvasc. Res. 40(30):327-340.

Gemmell, C.H. et al., "Utilization of a continuous flow reactor to study the lipoprotein-associated coagulation inhibitor (LACI) that inhibits tissue factor," (1990) Blood 76(11):2266-2271.

Gentry, R. et al., "Surface-mediated enzymatic reactions: simulations of tissue factor activation of factor X on a lipid surface," (1995) Biophys. J. 69(2):362-371.

Gerling, I. et al., "Multiple low-dose streptozocin-induced diabetes in NOD- scid/scid mice in the absence of functional lymphocytes," (1994) Diabetes 43:433-440.

Gill, R.G. et al., "CD4+ T cells are both necessary and sufficient for islet xenograft rejection," (1994), Transplantation Proceedings 26:1203.

Gir, S. et al., "A numerical analysis of factor X activation in the presence of tissue factor-factor VIIa complex in a flow reactor," (1996) Ann. Biomed. Eng. 24(3):394-399.

Gnanou, Y et al., "Synthesis of star-shaped poly(ethylene oxide)," (1998) Makromol. Chem. 189:2885-2892.

Goeden-Wood, N.L. et al., "Improved assembly of multimeric genes for the biosynthetic production of protein polymers," (Jul.-Aug. 2002) Biomacromolecules. 3(4):874-879.

Golden, M.A., "Healing of polytetrafluoroethylene arterial grafts is influenced by graft porosity," (1990) *J. Vascular Surgery* 11(6):838-844.

Goldsmith, H.L. and Turitto, V.T., "Rheological aspects of thrombosis and haemostasis: basic principles and applications," (1986) *Thromb. Haemostasis* 55(3):415-435.

Goosen, M.F.A. (1985), Optimization of microencapsulation parameters: semipermeable microcapsules as a bioartificial pancreas, *Biotech. Bioeng.* 27:146-150.

Goosen, M.F.A. et al., "Inactivation of thrombin by antithrombin III on a heparinized biomaterial," (1980) *Thrombosis Research* 20(5/6):543-554.

Grande, D. et al., "Glycosaminoglycan mimetic biomaterials. 2. Alkene- and acrylate-derivatized glycopolymers via cyanoxyl-mediated free-radical polymerization," (2001) *Macromolecules* 34:1640-1646 (tentatively published on Web Feb. 13, 2001).

Grande, D. et al., "Glycosaminoglycan mimetic biomaterials. 1. Nonsulfated and sulfated glycopolymers by cyanoxyl-mediated free-radical polymerization," (2000) *Macromolecules* 33:1123-1125.

Grande, D. et al., "Synthesis of non-sulfated and sulfated glycopolymers," (2000) *Polymer Preprints* 41(1):1000-1001.

Gray, W.R. et al., "Molecular model for elastin structure and function," (1973) *Nature* 246:461-466.

Gruber, A. et al., "Antithrombotic effects of combining activated protein C and urokinase in nonhuman primates," (1991) *Circulation* 84(6):2454-2462.

Gruber, A et al., "Inhibition of thrombus formation by activated recombinant protein C in a primate model of arterial thrombosis," (1990) *Circulation* 82(2):578-585.

Gruber, A. et al., "Inhibition of platelet-dependent thrombus formation by human activated protein C in a primate model," (1989) *Blood* 73(3):639-742.

Hall et al., "Factor Xa generation at the surface of cultured rat vascular smooth muscle cells in an in vitro flow system," (1998) *J. Biomech. Eng.* 120(4):484-490.

Hall, B. et al., "Biomembranes as models for polymer surfaces," (1989) *Biomaterials* 10(4):219-224.

Halle I., et al. (1993) "Protection of islets of Langerhans from antibodies by microencapsulation with alginate-poly-L-lysine membranes," *Transplantation*, 44:350-4.

Hanson, S.R. et al., "Blood flow and antithrombotic drug effects," (1998) *Am. Heart Journal* 135(5 Pt 2 Su):S132-145.

Hanson, S.R. et al., "Antithrombotic effects of thrombin-induced activation of endogenous protein C in primates," (1993) *J. Clin. Invest.* 92(4):2003-2012.

Hanson, S.R. et al., "Effects of angiotensin converting enzyme inhibition with cilazapril on intimal hyperplasia in injured arteries and vascular grafts in the baboon," (1991) *Hypertension* 18(4Suppl):II-70-II-76.

Hanson, S.R. et al., "Platelet interactions with Dacron vascular grafts; a model of acute thrombosis in baboons," (1985) *Arteriosclerosis* 5(6):595-603.

Harker, L.A. et al., "Effects of megakaryocyte growth and development factor on platelet production, platelet life span, and platelet function in healthy human volunteers," (Apr. 2000) *Blood* 95(8):2514-2522.

Hasegawa, T. et al., "Quantitative analysis of uniaxial molecular orientation in Langmuir-Blodgett films by infrared relection spectroscopy," (1995) *Langmuir* 11:1236-1243.

Haskins, K. and McDuffe, M. (1990), "Acceleration of diabetes in young NOD mice with CD4$^+$ islet-specific T cell clone," *Science* 249:1433-1436.

Hayashi, C.Y. et al., "Hypotheses that correlate the sequence, structure, and mechanical properties of spider silk proteins," (1999) *Int. J. Biol. Macromol.* 24:271-275.

Hayashi, C. Y. and Lewis, R. V., "Evidence from flagelliform silk cDNA for the structural basis of elasticity and modular nature of spider silks," (1998) *J. Mol. Biol.* 275: 773-84.

Hayward, J.A. et al., "Biomembranes as models for polymer surfaces," (1986) *Biomaterials* 7:252-258.

Hayward, J.A. and Chapman, D., "Biomembrane surfaces as models for polymer design: the potential for haemocompatibility,"(1984) *Biomaterials* 5:135-142.

Hayzer, D.J. et al., "cDNAs encoding the baboon thrombin receptor indicate a primate transcription start site upstream of putative sites reported for the human gene," (1999) *Throm. Res.* 98:195-201.

Hayzer, D.J. et al., "Characterization of a cDNA encoding the β-chain of baboon receptor glycoprotein GPIb" (1993) *Gene* 127:271-272.

Hébert, N. et al., "A new reagent for the removal of the 4-methozybenzyl ether: application to the synthesis of unusual macrocyclic and bolaform phosphatidylcholines," (1992) *J. Org. Chem.* 57:1777-1783.

Helm, C.A. et al., "Measurement of ligand-receptor interactions," (1991) *Proc. Natl. Acad. Sci. USA* 88:8169-8173.

Hergenrother, P.J. et al., "Small-molecule microarrays: covalent attachment and screening of alcohol-containing small molecules on glass slides," (2000) *J. Am. Chem. Soc.* 122:7849-7850.

Heroguez, V. et al., "Novel amphiphilic architectures by ring-opening metathesis polymerization of macromonomers," (1997) *Macromolecules* 30:4791-4798.

Huang, L. et al., "Generation of synthetic elastin-mimetic small diameter fibers and fiber networks," (2000) *Macromolecules* 33: 2989-2997 (published on Web Mar. 24, 2000).

Hubbell, J.A. et al., "Endothelial cell-selective materials for tissue engineering in the vascular graft via a new receptor," (1991) *Bio/Technology* 9:568-572.

Hudson, S.M., "The spinning of silk-like proteins into fibers," *Protein-Based Materials*, McGrath, K. and Kaplan, D., Ed.: Birkhauser: Boston, 1997, pp. 313-337.

Ishihara, K., "Novel polymeric materials for obtaining blood-compatible surfaces," (1997) *TRIP* 5(12):401-407.

Ishihara, K. et al., "Synthesis of phospholipid polymers having a urethane bond in the side chain as coating material on segmented polyurethane and their platelet adhesion-resistant properties," (1995) *Biomaterials* 16:873-879.

Ishihara, K. et al., "Hemocompatibility on graft copolymers composed of poly(2-methacryloxyethyl phosphorylcholine) side chain and poly(*n*-butyl methacrylate) backbone," (1994) *J. Biomed. Mater. Res.* 28:225-232.

Ishihara, K. et al., "Hemocompatibility of human whole blood on polymers with a phospholipid polar group and its mechanism," (1992) *J. Biomed Mat. Res.* 26:1543-1552.

Ishihara, K. et al., "Reduced thrombogenicity of polymers having phospholipid polar groups," (1990) *J. Biomed Mat. Res.* 24:1069-1077.

Jackson, R.L. et al., "Glycosaminoglycans: molecular properties, protein interactions, and role in physiological processes," (1991) *Physiol. Rev.* 71(2):481-539.

Janeway, C. and Bottomly, K., "Signals and signs for lymphocyte responses," (1994) *Cell* 76:275-285.

Jarpe, A.J. et al., "Flow cytometric enumeration of mononuclear cell populations infiltrating the islets of Langerhans in prediabetic NOD mice: Development of model of autoimmune insulinitis for Type I diabetes," (1990) *Regional Immunology* 3:305-317.

Kagan, H.M. et al., "Repeat polypeptide models of elastin as substrates for lysyl oxidase," (1980) *J. Biol. Chem.* 255:3656-3659.

Kalafatis, M. et al., "Regulation and regulatory role of γ-carboxyglutamic acid containing clotting factors," (1996) *Critical Reviews in Eukaryotic Gene Expression* 6(1):87-101.

Kalafatis, M. et al., "The regulation of clotting factors," (1997) *Crit. Rev. Eukaryotic Gene Expression* 7(3):241-280.

Kawamoto et al., "Reconstituted collagen is not capable of activating factor XII but causes intrinsic coagulation by activating platelets," (1992) *Blood Coagulation & Fibrinolysis* 3(4):371-379.

Ke, Y. et al., "Ovalbumin injected with complete Freund's adjuvant stimulates cytolytic responses," (1995) *Eur. J. Immunol.* 1995:549-553.

Khaled, Md. A. et al., "Proton magnetic resonance and conformational energy calculations of repeat peptides of tropoelastin: the tetrapeptide," (1976) *J. Am. Chem. Soc.* 98: 7547-7553.

Kim, D.H. et al., "The influence of tiered layers of surface-grafted poly(ethylene glycol) on receptor-ligand-mediated adhesion between phospholipid monolayer-stabilized microbubbles and coated glass beads," (2000) *Langmuir* 16:2808-2817.

Kim, H.S. et al., "Characterizing structural changes in point-bonded nonwoven fabrics during load-deformation experiments," (Feb. 2001) *Textile Res. J.* 71(2):157-164.

Kimura, T. et al., "High-resolution solid-state $^{13}$C nuclear magnetic resonance study of the combined process of $^1$H spin diffusion and $^1$H spin-lattice relaxation in semicrystalline polymers," (1992) *Polymer* 33(3):493-497.

King, G.A. et al (1987), "Alginate-polylysine microcapsules of controlled membrane molecular weight cutoff for mammalian cell culture engineering," *Biotech Progress* 3:231-240.

Kishida, A. et al., "In vivo and ex vivo evaluation of the antithrombogenecity of human thrombomodulin immobilized biomaterials," (1995) *ASAIO Journal* 41:M369-374.

Kishida, A. et al., "Immobilization of human thrombomodulin onto biomaterials," (1994) *ASAIO Journal* 40(3):M840-845.

Kishida, A. et al., "Immobilization of human thrombomodulin on biomaterials: evaluation of the activity of immobilized human thrombomodulin," (1994) *Biomaterials* 15(14):1170-1174.

Kishida, A. et al., "Immobilization of human thrombomodulin onto poly(ether urethane urea) for developing antithrombogenic blood-contacting materials," (1994) *Biomaterials* 15(10):848-852.

Kobayashi, T. et al., "Theory of the kinetics of reactions catalyzed by enzymes attached to membranes," (1974) *Biotech. Bioeng.* 16(1):77-97.

Kobayashi, T. et al., "Theory of the kinetics of reactions catalyzed by enzymes attached to the interior surfaces of tubes," (1974) *Biotech. Bioeng.* 16(1):99-118.

Köhler, A.S. et al., "Platelet adhesion to novel phospholipid materials: modified phosphatidylcholine covalently immobilized to silica, polypropylene, and PTFE materials," (1996) *J. Biomed. Mat. Res.* 32:237-242.

Kojima, M. et al., "Interaction between phospholipids and biocompatible polymers containing a phosphorylcholine moiety," (1991) *Biomaterials* 12:121-124.

Korbutt, G.S. et al., "Large scale isolation, growth, and function of porcine neonatal islet cells," (1996) *J. Clin. Invest.* 97(9):2119-2129.

Korbutt, G.S. et al., "Porcine islet cell antigens are recognized by xenoreactive natural human antibodies of both IgG and IgM subtypes," (1995) *Transplantation Proceedings* 28:821-823, pp. 837-838.

Korbutt, G.S. et al., "Successful reversal of diabetes in nude mice by transplantation of microencapsulated porcine neonatal islet cell aggregates," (1995) *Transplantation Proceedings* 27:3212.

Krejchi, M.T. et al., "Chemical sequence control of β-sheet assembly in macromolecular crystals of periodic polypeptides," (1994) *Science* 265:1427-1432.

Krych, M. et al., "Complement receptors," (1992) *Curr. Opin. Immunol.* 4:8-13.

Kuhlenschmidt, T.B. and Lee, Y.C., "Specificity of chicken liver carbohydrate binding protein," (1983) *Biochem.* 23(16):3569-3575.

Kühner, M. et al., "Lipid mono- and bilayer supported on polymer films: composite polymer-lipid films on solid substrates," (1994) *E. Biophys. J.* 67:217-226.

Lamparski et al. (1993) *J. Am. Chem. Soc.* 11:8096-8102.

Lamparski, H. et al., "Photoinduced destabilization of liposomes," (1992) *Biochemistry* 31:685-694.

Laster, J. and Silver, D., "Heparin-coated catheters and heparin-induced thrombocytopenia," (1988) *J. Vasc. Surg.* 7(5):667-672.

Lee, T.A.T. et al., "Thermo-reversible self-assembly of nanoparticles derived from elastin-mimetic polypeptides," (Aug. 2000) *Advanced Materials* 12(15):1105-1110.

Lenschow, D. et al. (1992), "Long-term survival of xenogeneic pancreatic islet grafts induced by CTLA4lg," *Science* 257:789-795.

Lim, F. and Sun, A.M. (1980), Microencapsulated islets as a bioartificial endocrine pancreas, *Science* 210:908-910.

Lindhout, T. et al., "Antithrombin activity of surface-bound heparin studied under flow conditions," (1995) *J. Biomed. Mater. Res.* 29(10):1255-1266.

Lindner, V. et al., "Basic fibroblast growth factor stimulates endothelial regrowth and proliferation in denuded arteries," (1990) *J. Clin. Invest.* 85:2004-2008.

Loudovaris, T. et al. (1992), "The role of T cells in the destruction of xenografts within cell impermeable membranes," *Transplantation Proceedings* 24:2938.

Loykulnant, S. and Hirao, A., "Protection and polymerization of functional monomers. 30. Anionic living polymerization of 4-alkylstyrenes containing acetal-protected monosaccharide residues," (2000), *Macromolecules* 33:4757-4764.

Loykulnant, S. et al., "Protection and polymerization of functional monomers. 28. Anionic living polymerization of styrene derivatives containing acetal-protected monosaccharide residues," (1998) *Macromolecules* 31:9121-9126.

Lu, D. et al., "Comparison of activated protein C/protein S-mediated inactivation of human factor VIII and factor V," (1996) *Blood* 87(11):4708-4717.

Lvov, Y. et al., "Assembly, structural characterization, and thermal behavior of layer-by-layer deposited ultrathin films of poly(vinyl sulfate) and poly(allylamine)," (1993) *Langmuir* 9:481-486.

MacDonald, R.C. et al., "Small-volume extrusion apparatus for preparation of large, unilamellar vesicles," (1991) *Biochim. Biophys. Acta* 1061:297-303.

Mann, K.G. et al., "Cofactor proteins in the assembly and expression of blood clotting enzyme complexes," (1988) *Ann. Rev. Biochemistry* 57:915-956.

Mao, G., et al., "Interactions, structure, and stability of photoreactive bolaform amphiphile multilayers," (1995) *Langmuir* 11:942-952.

Maoz et al. (1984) "On the formation and structure of self-assembling monolayers," *J. Colloid Interface Sci.* 100(2):456.

Markovich, R.J. et al., "Silica subsurface amine effect on the chemical stability and chromatographic properties of end-capped immobilized artificial membrane surfaces," (1991) *Anal. Chem.* 63:1851-1860.

Marra, K.G. et al., "Cytomimetic biomaterials. 1. In-Situ polymerization of phospholipids on an alkylated surface," (1997) *Macromolecules* 30:6483-6488.

Marra, K.G. et al., "Cytomimetic biomaterials. 2. In-Situ polymerization of phospholipids on a polymer surface," (1997) *Langmuir* 13:5697-5701.

Marra, K.G. et al., "Stabilized phosphatidylcholine surfaces via in-situ polymerization at a solid-liquid interface," (1997) *Polymer Preprints* 38(2):682-683.

Marsh, A. et al., "Atom transfer polymerization: use of uridine and adenosine derivatized monomers and initiators," (1999) *J. Macromolecules* 32:8725-8731.

Martin, D.C. et al., "Processing and Characterization of Protein Polymers," *Protein-Based Materials*, McGrath, K. and Kaplan, D., Ed.; Birkhauser: Boston, 1997, pp. 339-370.

Martin, S.F. et al., "General method for the synthesis of phospholipid derivatives of 1,2-O-diacyl-sn-glycerols," (1994) *J. Org. Chem.* 59:4805-4820.

Massia, S.P. and Hubbell, J.A., "Vascular endothelial cell adhesion and spreading promoted by the peptide REDV of the IIICS region of plasma fibronectin is mediated by integrin $\alpha_2\beta_7$," (1992) *J. Biol. Chem.* 267:14019-14026.

Matthew, H.W. et al (1993) "Complex coacervate microcapsules for mammalian cell culture and artificial organ development," *Biotechnol. Prog.* 9:510-519.

Mauk, A.W. et al., "Structural characterization of self-assembled lipid monolayers by N$\pi$T simulation," (1998) *Langmuir* 14:5255-5266.

Mauk, M.R. et al., "Vesicle targeting: timed release and specificity for leukocytes in mice by subcutaneous injection," (1980) *Science* 207:309-311.

McLean, L.R. et al., "Preparation of stable polar surfaces using polymerizable long-chain diacetylene molecules," (1983) *Thin Solid Films* 99:127-131.

McMillan R.A. and Conticello, R. P., "Synthesis and characterization of elastin-mimetic protein gels derived from a well-defined polypeptide precursor," (2000) *Macromolecules* 33:4809-4821.

McMillan, R.A. et al., "High-resolution topographic imaging of environmentally responsive, elastin-mimetic hydrogels," (1999) *Macromolecules* 32:9067-9070.

McMillan, R.A. et al., "Rapid assembly of synthetic genes encoding protein polymers," (1999) *Macromolecules* 32: 3643-3648.

McPherson, D.T. et al., "Product purification by reversible phase transition following *Escherichia coli* expression of genes encoding up to 251 repeats of the elastomeric pentapeptide GVGVP," (1996) *Protein Expression Purification* 7: 51-57.

McPherson, D.T. et al., "Production and purification of a recombinant elastomeric polypeptide, G-(VPGVG)$_{19}$-VPGV, from *Escherichia coli*," (1992) *Biotechnology Progress* 8:347-352.

Merrill, E.W. et al., "Polyvinyl alcohol-heparin hydrogel 'G'," (1970) *J. Applied Physiology* 29(5):723-730.

Meuse, C. W. et al., "Hybrid bilayer membranes in air and water: infrared spectroscopy and neutron reflectivity studies," (1998) *Biophys J.* 74:1388-1398.

Mielczarski, J.A. and Yoon, R.H., "Fourier transform infrared external reflection study of molecular orientation in spontaneously adsorbed layers on low-absorption substrates," (1989) *J. Phys. Chem.* 93:2034-2038.

Miller, B. et al., "Both the Lyt-2$^+$ and L3T4$^+$ T cell subsets are required for the transfer of diabetes in nonobese diabetic mice" (1988) *J. Immunol.* 140:52-8.

Minoda, M. et al. "Synthesis of functional polymers bearing pendant mono- and oligo- saccharide residues," *Macromol. Symp.* 99:169-177 (1995).

Miyata, T. and Nakamae, K., "Polymers with pendant saccharides—'glycopolymers'," (1997) *Trends Polym. Sci.* 5:198-206.

Miyoshi, M. et al., "A rapid formation of lysine-derived crosslinks by chick embryo aorta," (1976) *J. Biochem.* (Tokyo) 79: 235-1243.

Monshipouri, M. and Rudolph, A.S., "Liposome-encapsulated alginate: controlled hydrogel particle formation and release," (1995) *J. Microencapsulation* 12(2):117-127.

Moses, R. et al. (1990), "Xenogeneic proliferation and lymphokine production are dependent upon CD4+ helper T cells and self antigen-presenting cells in the mouse. I," *Exp. Med.* 172:567-75.

Moya, S. et al., "Lipid coating on polyelectrolyte surface modified colloidal particles and polyelectrolyte capsules," (2000) *Macromolecules* 33:4538-4544.

Müller-Eberhard, H.I., "Molecular organization and function of the complement system," (1988) *Ann. Rev. Biochem.* 57:321-347.

Nagahori, N. and Nishimura, S-I., "Tailored glycopolymers: controlling the carbohydrate-protein interaction based on template effect," (2001) *Biomacromolecules* 2:22-24 (published on Web Dec. 28, 2000).

Nagle, J.F. et al., "X-ray structure determination of fully hydrated $L_\alpha$ phase dipalmitoylphosphatidylcholine bilayers," (1996) *Biophys. J.* 70:1419-1431.

Nah, J-W et al., "Polymeric micelle formation of multiblock copolymer composed of poly(γ-benzyl *L*-glutamate) and poly(ethylene oxide)," (2000) *Bull. Korean Chem. Soc.* 21(4):383-388.

Nah, J-W et al., Drug-delivery system based on core-shell-type nanoparticles composed of poly(γ-benzyl *L*-glutamate) and poly(ethylene oxide), (2000) *J. App. Polymer Sci.* 75:115-1126.

Nemerson, Y. and Turitto, V.T., "The effect of flow on hemostasis and thrombosis," (1991) *Thromb. Haemostasis* 66(3):272-276.

Nickerson, P. et al., "Analysis of cytokine transcripts in pancreatic islet cell allografts during rejection and tolerance induction," (1993) *Transplantation Proceedings* 25:984-985.

Nojiri, C. et al., "Can heparin immobilized surfaces maintain nonthrombogenic activity during In Vivo long-term implantation?" (1996) *ASAIO Journal* 42(5):M468-475.

Nojiri, C. et al., "In vivo nonthrombogenicity of heparin immobilized polymer surfaces," (1990) *ASAIO Transactions* 36(3):M168-172.

Nomura, K. and Schrock, R.R., "Preparation of 'sugar-coated' homopolymers and multiblock ROMP copolymers," (1996) *Macromolecules* 29:540.

O'Brien, D.F. et al., "Polymerization of preformed self-organized assemblies," (1998) *Acc. Chem. Res.* 31:861-868.

O'Connell, P.J. et al., "Unmodified pancreatic islet allograft rejection results in the preferential expression of certain T cell activation transcripts," (1993) *J. Immunol.* 150:1093-1104.

O'Donnell, J. H. and Whittaker, A. K., "Radiation degradation of linear low density polyethylene: determination of lamellae thickness, crystallinity and crosslinking by solid-state $^{13}$C NMR and DSC," (1992) *Radiat. Phys. Chem.* 36(20:209-214.

O'Donnell, J. H. and Whittaker, A. K., "A solid-state $^{13}$C-NMR study of crosslinking in polybutadiene by γ radiation: effect of microstructure and dose," (1992) *J. Polym. Chem. Ed.* 30:185-195.

Ohno, K. et al., "Nitroxide-controlled free radical polymerization of a sugar-carrying acryloyl monomer," (1999) *Macromol. Chem. Phys.* 200:1619-1625.

Ohno, K. et al., "Synthesis of a well-defined glycopolymer by nitroxide-controlled free radical polymerization," (1998) *Macromolecules* 31:1064.

Ohno, K. et al., "Synthesis of a well-defined glycopolymer by atom transfer radical polymerization," (1998) *J. Polym. Sci., Part A: Polym. Chem.* 36:2473-2481.

Ohno, K. et al., "Free radical polymerization of a sugar residue-carrying styryl monomer with a lipophilic alkoxyamine initiator: synthesis of a well-defined novel glycolipid," (1998) *Macromol. Chem. Phys.* 199:2193-2197.

Ohno, H. et al., "Polymerization of liposomes composed of diene-containing lipids by UV and radical initiators: evidence for the different chemical environment of diene groups on 1- and 2-acyl chains," (1987) *Macromol.* 20:929-933.

Ohno et al., "Polymerization of liposomes composed of diene-containing lipids by radical initiators. II. Polymerization of monodiene-type lipids as liposomes," (1987) *J. Polym. Sci.: Part A: Polym. Chem.* 25:2737-2746.

Orban, J.M. et al., "Cytomimetic biomaterials. 4. In-situ photo polymerization of phospholipids on an alkylated surface," (2000) *Macromolecules* 33:4205-4212 (published on Web May 6, 2000).

Ornitz, D.M. et al., "FGF binding and FGF receptor activation by synthetic heparan-derived di- and trisaccharides," (1995) *Science* 268:432-434.

Otani et al., "Rapidly curable biological glue composed of gelatin and poly(L-glutamic acid)," (1996) *Biomaterials* 17(14):1387-1391.

Owen, W.G. and Esmon, C.T., "Functional properties of an endothelial cell cofactor for thrombin-catalyzed activation of protein C," (1981) *J. Biol. Chem.* 256(11):5532-5535.

Packer, K. J. et al., "The effects of morphology on $^1$H NMR spectra and relaxation in semicrystalline polyolefins," (1984) *J. Polym. Sci.: Polym. Phys.* 22:589-616.

Panitch, A. et al., "Design and biosynthesis of elastin-like artificial extracellular matrix proteins containing periodically spaced fibronectin CS5 domains," (1999) *Macromolecules* 32:1701-1703.

Parikh, A.N. et al., "An intrinsic relationship between molecular structure in self-assembled *n*-alkylsiloxane monolayers and deposition temperature," (1994) *J. Phys. Chem.* 98:7577.

Parker, W. et al., "Transplantation of discordant xenografts: a challenge revisited," (1996) *Immunology Today* 17:373-378.

Pasquali-Ronchetti et al., "Study of elastic fiber organization by scanning force microscopy," (1998) *Matrix Biology* 17:75-83.

Pasquali-Ronchetti et al., "Ultrastructure of elastin," (1995) *Ciba Foundation Symposium* 192:31-50.

Pearce, K.H. et al., "Comparison of the membrane binding kinetics of bovine prothrombin and its fragment 1," (1993) *J. Biol. Chem.* 268:22984-22991.

Peterson, I.D., and Haskins, K. (1996), "Transfer of diabetes in the NOD-*scid* mouse by CD4 T-cell clones: differential requirement for CD8 T-cells," *Diabetes* 45:328-36.

Petka, W.A. et al., "Reversible hydrogels from self-assembling artificial proteins," (1998) *Science* 281:389-392.

Petitou, M. et al., "Synthesis of thrombin-inhibiting heparin mimetics without side effects," (1999) *Nature* 398:417-422.

Petitou, M. et al., "First synthetic carbohydrates with the full anticoagulant properties of heparin," (1998), *Chem. Int. Ed.* 37:3009-3014.

Pierson, R. et al. (1989), "CD4+ lymphocytes play a dominant role in murine xenogeneic responses," *Transplantation Proceedings* 21:519.

Plant, A.L. et al., "Phospholipid/alkanethiol bilayers for cell-surface receptor studies by surface plasmon resonance," (1995) *Anal. Biochem.* 226:342-348.

Plant, A. L., "Self-assembled phospholipid/alkanethiol biomimetic bilayers on gold," (1993) *Langmuir* 9: 2764-2767.

Plant, A.L. et al., "Generic liposome reagent for immunoassays," (1989) *Anal. Biochem.* 176:420-426.

Ponpipom, M.M. and Bugianesi, R.L., "Isolation of 1,3-distearoyl-glycero-2-phosphocholine (β-lecithin) from commercial 1,2-distearoyl-sn-glycero-3-phosphocholine," (1980) *Lipid Res.* 21:136-139.

Pourdeyhimi, B. et al., "Measuring fiber diameter distribution in nonwovens," (1999) *Textile Res. J.* 69:233-236.

Qiu, Z-H. and Leslie, C.C., "Protein kinase C-dependent and -independent pathways of mitogen-activated protein kinase activation in macrophages by stimuli that activate phospholipase $A_2$," (1994) *J. Biol. Chem.* 269:19480-19487.

Rand, M.D. et al., "Blood clotting in minimally altered whole blood," (1996) *Blood* 88(9):3432-3445.

Rapaka, R.S. et al., "Non-elastomeric polypeptide models of elastin," (1978) *Int. J. Pept. Protein Res.* 11:109-127.

Regen, S.L. et al., "Polymer-supported membranes. A new approach for modifying polymer surfaces," (1983) *Macromolecules* 16:335-338.

Reneker, D.H. and Chun, I., "Nanometre diameter fibres of polymer, produced by electrospinning," (1996) *Nanotechnology* 7: 216-223.

Reneker, D.H. and Srinivasan, G., "Electrospun polyaramid fibers: structure and morphology," (1995) *Bull Am. Phys. Soc.* 40:351.

Rifkin, D.B. and Moscatelli, D., "Recent developments in the cell biology of basic fibroblast growth factor," (1989) *J. Cell. Biol.* 109:1-6.

Ringsdorf et al., "Molecular architecture and function of polymeric oriented systems: models for the study of organization, surface recognition, and dynamics of biomembranes," (1988) *Angew. Chem. Int. Ed. Engl.* 27:113-158.

Roach, M.R. and Burton A.C., "The reason for the shape of the distensibility curves of arteries," (1957) *Can. J. Biochem. Physiol.* 35:681-690.

Roberts, I. et al. (1996), "Dopamine secretion by PC12 cells microencapsulated in a hydroxymethyl methacrylate-methyl methacrylate copolymer," *Biomaterials* 17:267-275.

Robins, S. P., "Analysis of the crosslinking components in collagen and elastin," (1982) *Methods Biochem. Anal.* 28:329-379.

Roy, B.C. et al., "Synthesis and fluorescence properties of new fluorescent, polymerizable, metal-chelating lipids," (2000) *J. Org. Chem.* 65:3644-3651.

Roy, R., "Recent developments in the rational design of multivalent glycoconjugates," (1997) *Topics in Current Chem.* 187:241-274.

Roy, R., "Syntheses and some applications of chemically defined multivalent glycoconjugates," (1996) *Current Opinion in Structural Biology* 6:692-702.

Sabatani, E. and Rubinstein, I., "Organized self-assembling monolayers on electrodes. 2. Monolayer-based ultramicroelectrodes for the study of very rapid electrode kinetics," (1987) *J. Phys. Chem.* 91:6663-6669.

Sackmann, R. and Tanaka, M., Supported membranes on soft polymer cushions: fabrication, characterization and applications, (2000) *Trans Biotechnol.* 18:58-64.

Sadler, J.E., "Thrombomodulin structure and function," (1997) *Thromb. Haemostasis* 78(1):392-395.

Sakai, H. and Umemura, J., "Molecular orientation in Langmuir films of 12-hydroxystearic acid studied by infrared external-reflection spectroscopy," (1998) *Langmuir* 14:6249-6255.

Sakata, Y., et al., "Activated protein C stimulates the fibrinolytic activity of cultured endothelial cells and decreases antiactivator activity," (1985) *Proc. Natl. Acad. Sci. USA* 82(4):1121-1125.

Sandberg, L.B. et al., "Elastin covalent structure as determined by solid phase amino acid sequencing," (1985) *Pathol. Biol.* 33:266-274.

Sandberg, L.B. et al., "Elastin structure, biosynthesis, and relation to disease states," (1981) *N. Engl. J. Med.* 304:566-579.

Sandberg, L.B. et al., "Primary structure of porcine tropoelastin," (1977) *J. Adv. Exp. Med. Biol.* 79:277-284.

Santin, M. et al., "Synthesis and characterization of a new interpenetrated poly(2-hydroxyethylmethacrylate)-gelatin composite polymer," (1996) *Biomaterials* 17(15):1459-1467.

Sato, Y. and Rifkin, D.B., "Autocrine activities of basic fibroblast growth factor: regulation of endothelial cell movement, plasminogen activator synthesis, and DNA synthesis," (1988) *J. Cell. Biol.* 107:1199-1205.

Scmidt, R.R., "Recent developments in the synthesis of glycoconjugates," (1989) *Pure Appl. Chem.* 61(7):1257-70.

Sefton, M.V., (1989), *Can. J. Chem. Eng.* 67:705-712.

Seifert, K. et al., "Charge transport by ion translocating membrane proteins on solid supported membranes," (1993) *Biophys. J.* 64:384-391.

Seitz, M. et al., "Formation of tethered supported bilayers via membrane-inserting reactive lipids," (1998) *Thin Solid Films* 329:767-771.

Sells, T.D. & O'Brien, D.F., "Two-dimensional polymerization of lipid bilayers: degree of polymerization of acryloyl lipids," (1994) *Macromolecules* 27:226-233.

Shen, W. W. et al., "Polymer-supported lipid bilayers on benzophenone-modified substrates," (2001) *Biomacromolecules* 2:70-79.

Shi, X. and Caruso, F., "Release behavior of thin-walled microcapsules composed by polyelectrolyte multilayers," (2001) *Langmuir* 17:2036-2042.

Shoji, M. et al., "Human and baboon integrin $β_5$ subunit-encoding mRNAs have alternative polyadenylation sites," (1993) *Gene* 133:307-308.

Shultz, L. et al., "Multiple defects in innate and adaptive immunologic function in NOD/LtSz-*scid* mice," (1995) *J. Immunology* 154:180-191.

Siedlecki, C.A. et al., "Interactions of human von Willebrand factor with a hydrophobic self-assembled monolayer studied by atomic force microscopy," (1994) *Biomed. Mater. Res.* 28:971.

Slack, S.M. et al., "The effects of flow on blood coagulation and thrombosis," (1993) *Thromb. Haemostasis* 70(1):129-134.

Slack, S.M. and Turitto, V.T., "Flow chambers and their standardization for use in studies of thrombosis," (1994) *Thromb. Haemostasis* 72(5):777-781.

Smirnov, M.D. et al., "The effect of membrane composition on the hemostatic balance," (1999) *Biochemistry* 38(12):3591-3598.

Smirnov, M.D. and Esmon, C.T., "Phosphatidylethanolamine incorporation into vesicles selectively enhances factor Va inactivation by activated protein C," (1994) *J. Biol. Chem.* 269(2):816-819.

Snyder, R.G. et al., "Vibrational spectra in the C—H stretching region and the structure of the polymethylene chain," (1978) *Spectrochim. Acta, Part A* 34A:395-406.

Solletti, J.M. et al., "Elaboration and characterization of phospholipid Langmuir-Blodgett films," (1996) *Langmuir* 1:5379-5386.

Spinke, J. et al., "Polymer-supported bilayer on a solid substrate," (1992) *Biophys. J.* 63:1667-1671.

Stoll, M.S. et al., "Improved procedure for the construction of neoglycolipids having antigenic and lectin-binding activities, from reducing oligosaccharides," (1988) *Biochemical J.* 256:661-664.

Sun, F. et al., "Ultrathin self-assembled polymeric films on solid surfaces. 2. Formation of 11-(*n*-pentyldithio)undecanoate-bearing polyacrylate monolayers on gold," (1993) *Langmuir* 9:3200-3207.

Sun, F. et al., "Spontaneous polymer thin film assembly and organization using mutually immiscible side chains," (1996) *J. Am. Chem. Soc.* 118:1856-1866.

Sun, F. et al., "Ultrathin self-assembled polymeric films on solid surfaces. III. Influence of acrylate dithioalkyl side chain length on polymeric monolayer formation on gold," (1994) *J. Vac. Sci. Technol.* 12:2499.

Sun, L. and Chaikof, E.L., "The synthesis of neoglycophospholipid conjugates via reductive amination of ω-oxoalkylglycosides and phosphatidylethanolamines," (1998) *Carbohydrate Res.* 370:77-81.

Sun, L. and Chaikof, E.L., "Neoglycophospholipids with alkyl spacers: synthesis via an improved reductive amination and monolayer properties," (1997) *Bioconjugate Chem.* 8:567-571.

Sun, Y. et al. (1996), "Normalization of diabetes in spontaneously diabetic cynomologus monkeys by xenografts of microencapsulated porcine islets without immunosuppression," *J. Clin. Invest.* 98:1417-1422.

Takeuchi, T. et al. (1992), "Heart allografts in murine systems: The differential activation of Th2-like effector cells in peripheral tolerance," *Transplantation* 53:1281-1294.

Tasumi, M.S. and Miyaza, T.J., "Normal vibrations and force constants of polymethylene chain," (1962) *J. Mol. Spectrosc.* 9:261-287.

Tendian, S.W. et al., "Evidence from total internal reflection fluorescence microscopy for calcium-independent binding of prothrombin to negatively charged planar phospholipid membranes," (1991) *Biochemistry* 30:10991-10999.

Terranova, V.P. et al., "Human endothelial cells are chemotactic to endothelial cell growth factor and heparin," (1985) *Cell Biol.* 101:2330-2334.

Thomas, G.J. and Prescott, B., "Raman amide bands of type-II β-turns in cyclo-(VPGVG)$_3$ and poly-(VPGVG), and implications for protein secondary-structure analysis," (1987) *Biopolymers* 26:921-934.

Toshima, K. and Tatsuta, K., "Recent progress on O-glycosylation methods and its application to natural products synthesis," (1993) *Chem. Rev.* 93:1503-1531.

Turitto, V.T. and Hall, C.L., "Mechanical factors affecting hemostasis and thrombosis," (1998) *Thromb. Res.* 92(6 Suppl. 2):S25-310.

Ueda, T. et al., "Preparation of 2-methacryloyloxyethyl phosphorylcholine copolymers with alkyl methacrylates and their blood compatibility," (1992) *Polym. J.* 24(11):1259-1269.

Uludag, H. and Sefton, M.V., "Metabolic activity and proliferation of CHO cells in hydroxyethyl methacrylate-methyl methacrylate (HEMA-MMA) microcapsules," (1993) *Cell Transplantation* 2:175-182.

Urry, D.W. et al., "Protein-based materials with a profound range of properties and applications: the elastin δT$_t$ hydrophobic paradigm," K. McGrath and D. Kaplan, Ed., Birkhauser: Boston, (1997), pp. 133-177.

Urry, D.W. et al., "Molecular biophysics of elastin structure, function and pathology," (1995) *Ciba Foundation Symposium* 192:4-30.

Urry, D.W., "Molecular machines: how motion and other functions of living organisms can result from reversible chemical changes," (1993) *Angew. Chem. Int. Ed. Engl.* 32:819-841.

Urry, D.W. et al., "Two-dimensional proton NMR studies on poly(VPGVG) and its cyclic conformational correlate, cyclo(VPGVG)$_3$," (1989) *Biopolymers* 28:819-833.

Urry, D.W., "Entropic elastic processes in protein mechanisms. I. Elastic structure due to an inverse temperature transition and elasticity due to internal chain dynamics," (1988) *J. Prot. Chem.* 7(1):1-34.

Urry, D.W. et al., "Polytetrapeptide of elastin," (1986) *Int. J. Pept. Protein Res.* 28:649-660.

Urry, D.W. et al., "Polypentapeptide of elastin: temperature dependence of ellipticity and correlation with elastomeric force," (1985) *Biochem. Biophys. Res. Commun.* 130:50-57.

Urry, D.W. et al., "Phase-structure transitions of the elastin polypentapeptide-water system within the framework of composition-temperature studies," (1985) *Biopolymers* 24:2345-2356.

Urry, D.W. et al., "Studies on the conformation and interactions of elastin secondary structure of synthetic repeat hexapeptides," (1975) *Biochim. Biophys. Acta* 393:296-306.

Urry, D.W. et al., "Studies on the conformation and interactions of elastin. Proton magnetic resonance of the repeating pentapeptide," (1974) *Biochemistry* 13:609-616.

van Ackern, F. et al., Ultrathin membranes for gas separation and pervaporation prepared upon electrostatic self-assembly of polyelectrolytes, (998) *Thin Solid Films* 329:762-766.

Van Boeckel, C.A.A. et al., "the unique antithrombin III binding domain of heparin: a lead to new synthetic antithrombotics," (1993) *Chem. Int. Ed. Engl.* 32(12):1671-1690.

Van Den Bulcke, A.I. et al., "Structural and rheological properties of methacrylamide modified gelatin hydrogels," (2000) *Biomacromolecules* 1:31-38.

Vanderhart, D. L., "Proton spin diffusion as a tool for characterizing polymer blends," (1990) *Makromol. Chem., Macromol. Symp.* 34:125-159.

van't Veer, C. et al., "Inhibitory mechanism of the protein C pathway on tissue factor-induced thrombin generation," (1997) *J. Biol. Chem.* 272(12):7983-7984.

Vasilets, V.N. et al., "Microwave $CO_2$ plasma-initiated vapour phase graft polymerization of acrylic acid onto polytetrafluoroethylene for immobilization of human thrombomodulin," (1997) *Biomaterials* 18(17):1139-1145.

Viitala, T. et al., "Protein immobilization to a partially cross-linked organic monolayer," (2000) *Langmuir* 16:4953-4961.

Wall, R.T. et al., "Human endothelial cell migration: stimulation by a released platelet factor," (1978) *Lab Invest.* 39(5):523-529.

Wang, P. et al., "Synthesis of phospholipid-inhibitor conjugates by enzymatic transphosphatidylation with phospholipase D," (1993) *J. Am. Chem. Soc.* 115:10487-10491.

Wasserman, Z.R. and Salemme, F.R., "A molecular dynamics investigation of the elastomeric restoring force in elastin," (1990) *Biopolymers* 29:1613-1631.

Wasserman, S.R. et al., "The structure of self-assembled monolayers of alkylsiloxanes on silicon: a comparison of results from ellipsometry and low-angle X-ray reflectivity," (1989) *J. Am. Chem. Soc.* 111:5852-5861.

Weber, C.J. et al., "CTLA4-lg prolongs survival of microencapsulated neonatal porcine islet xenografts in diabetic NOD mice," (1997) *Cell Transplantation* 6(5):505-508.

Weber, C. et al. (1994), "NOD mouse peritoneal cellular response to poly-L-lysine-alginate microencapsulated rat islets," *Transplantation Proceedings* 26:1116-1119.

Weber, C. et al. (1990), "Microencapsulated dog and rat islet xenografts into streptozotocin-diabetic and NOD mice," *Horm. Metab. Res.* 35:219-226.

Weber, C.I. et al. (1990), "The role of $CD4^+$ helper T cells in destruction of microencapsulated islet xenografts in NOD mice," *Transplantation* 49(2):396-404.

Weiner, A.L. et al., (1985), "Liposome-collagen gel matrix: A novel sustained drug delivery system," *J. Pharm. Sci.* 74(9):922-925.

Welsh, E. R. and Tirrell, D. A., "Engineering the extracellular matrix: A novel approach to polymeric biomaterials. I. Control of the physical properties of artificial protein matrices designed to support adhesion of vascular endothelial cells," (2000) *Biomacromolecules* 1:23-30.

Westerduin, P. et al., "Synthesis of tailor-made glycoconjugates showing AT III-mediated inhibition of blood coagulation factors Xa and thrombin," (1996) *Chem. Int. Ed. Engl.* 35:331-333.

Westman, J. et al., "Synthesis and fibroblast growth factor binding of oligosaccharides related to heparin and heparan sulphate," (1995) *J. Carbohydr. Chem.* 14:95-113.

Wick et al., "Unusually large von Willebrand factor multimers increase adhesion of sickle erythrocytes to human endothelial cells under controlled flow," (1987) *J. Clin. Invest.* 80:905-910.

Wilbur, D.S. et al., "Biotin reagents for antibody pretargeting. 4. Selection of biotin conjugates for in vivo application based on their dissociation rate from avidin and streptavidin," (2000) *Bioconjugate Chem.* 11:569-583.

Winger, T.M. et al., "Formation and stability of complex membrane-mimetic monolayers on solid supports," (1999) *Langmuir* 15:3866-3874.

Winger, T.M. and Chaikof, E.L., "Synthesis and characterization of supported phospholipid monolayers: a correlative investigation by radiochemical titration and atomic force microscopy," (1998) *Langmuir* 14:4148-4155.

Winger, T.M. and Chaikof, E.L., "Synthesis and characterization of supported bioactive lipid membranes," In: *Materials Science of the Cell*, A. Plant and V. Vogel (Ed.), MRS Publications, Pittsburgh (1998), pp. 113-118.

Winger T.M. et al., "Behavior of lipid-modified peptides in membrane-mimetic monolayers at the air/water interface," (1997) *Langmuir* 13:3256-3259.

Winger T.M. et al., Lipopeptide conjugates: Biomolecular building blocks for receptor activating membrane-mimetic structures. (1996) *Biomaterials* 17:443-449.

Winger, T.M. et al., "A convenient route to thiol terminated peptides for conjugation and surface functionalization strategies," (1995) *Bioconjug. Chem.* 6:323-326.

Winger, T.M. et al., Purification of synthetic lipopeptide conjugates by liquid chromatography, (1995) *J. Liquid Chromatogr.* 18:4117-4125.

Wong, J.S. & Yen, Y.S., "Intriguing absorption band behavior of IR reflectance spectra of silicon dioxide on silicon," (1988) *Appl. Spectrosc.* 42(4):598-604.

Wright, E.R. and Conticello, V.P., "Self-assembly of block copolymers derived from elastin-mimetic polypeptide sequences," (Oct. 2002) *Adv. Drug Deliv. Rev.* 54(8):1057-1073.

Wright, E.R. et al., "Thermoplastic elastomer hydrogels via self-assembly of an elastin-mimetic triblock polypeptide," (Feb. 2002) *Adv. Funct. Mater.* 12:149-154.

Xiao, X-D et al., "Preparation, structure, and mechanical stability of alkylsilane monolayers on mica," (1995) *Langmuir* 11(5):1600-1604.

Yamada, K. et al., "Controlled synthesis of amphiphilic block copolymers with pendant N-acetyl-D-glucosamine residues by living cationic polymerization and their interaction with WGA lectin," (1999) *Macromolecules* 32:3553.

Yamada, K. et al., "Controlled synthesis of glycopolymers with pendant D-glucosamine residues by living cationic polymerization," (1997) *J. Polym. Sci. Part A: Polym. Chem.* 35:751-757.

Yen, Y.-S. and Wong, J. (1989) *J. Phys. Chem.* 93:7208-7216.

Yoshioko, T. et al., "Encapsulation of mammalian cell with chitosan-CMC capsule," (1990) *Biotechnol. Bioeng.* 35:66-72.

Yu, S.M. et al., "Smectic ordering in solutions and films of a rod-like polymer owing to monodispersity of chain length," (1997) *Nature* 389:167-170.

Zhang, H. et al., "Synthesis of 4% glu-containing Val[1] and Ile[1]-polypentapeptides: model protein systems for demonstrating mechanochemical coupling," (1989) *J. Protein Chem.* 8:173-182.

Zierler et al., "Accuracy of duplex scanning for measurement of arterial volume flow," (1992) *J. Vasc. Surg.* 16(4):520-526.

Ejaz, M. et al. (2000) Macromolecules 33:2870.

Frank, M. and Ries, L. F. "The role of complement in inflammation and phagocytosis," (1991) *Immunol. Today* 12:322-326.

Ito, Y., Section/Chapter 5.2, "Cell growth factor immobilized materials," p. 285-310, in Imanishi, Y. 1991. Synthesis of Biocomposite Materials: Chemical and Biological Modified Natural Polymers, Boca Raton, FL, CRC Press, 314 p. ISBN 0849367719.

Moore et al. (1983) Macromolecules 16:335-338.

Rosen, E. M. et al. "Regulation of motility in bovine brain endothelial cells," (1991) J. Cell Physiol. 146:325-335.

Serruys, P. W. et al., "Randomised comparison of implantation of heparin-coated stents with balloon angioplasty in selected patients with coronary artery disease (Benestent II)," (1998) Lancet 352:673-681.

Weber, C. J. et al., "Encapsulated islet iso-, allo-, and xenografts in diabetic NOD mice," (1995) Transplantation Proceedings 27:3308-3311.

GLYCOPOLYMERS AND FREE RADICAL POLYMERIZATION METHODS

STATEMENT REGARDING FEDERALLY SPONSORED RESEARCH OR DEVELOPMENT

This invention was made with government support under NIH Contract No. RO1HL60464 awarded by the National Institutes of Health. The government has certain rights in the invention.

CROSS-REFERENCE TO RELATED APPLICATIONS

This invention claims priority to U.S. Ser. No. 60/261,275 filed Jan. 12, 2001, which is fully incorporated herein by reference to the extent not inconsistent herewith.

BACKGROUND

Glycosaminoglycans (GAGs) are naturally occurring linear polysaccharides encountered both in the extracellular matrix and on cell surfaces where they form a carbohydrate coating referred to as the glycocalyx. GAGs are involved in a wide array of physiological processes, including cell proliferation and migration, as well as modulation of angiogenesis and inflammatory responses (Clowes, A. W. and Karnovsky, M. S. (1977) *Nature* 265; Jackson, R. L. et al. (1991) *Physiol. Rev.* 71:481; Linhardt, R. J. et al. (1996) In *Biomedical Functions and Biotechnology of Natural and Artificial Polymers*, ATL Press, p. 45). The diverse bioactivities of GAGs are a consequence of unique binding sequences that facilitate local sequestration of biologically active proteins, such as growth factors and antithrombin III. In this manner, GAGs function as delivery vehicles for the controlled local release of a variety of proteins and; in select circumstances, potentiate the activity of the bound protein (Kjellen, L. and Lindahl, U. (1991) *Ann. Rev. Biochem.* 60:443; Faham, S. et al. (1996) *Science* 271:1116; Bitomsky, W. and Wade, R. C. (1999) *J. Am. Chem. Soc.* 121:3004). Glycopolymers can induce affinity toward proteins such as lectins, and to viruses, due to multivalent recognition, known as the "cluster effect." (Lee, Y. C. and Lee, R. T., Eds. (1994) *Neoglycoconjugates: Preparation and applications*; Academic Press, San Diego, Calif.; Roy, R. (1996) *Current Opinion in Structural Biology* 6:692–702.)

The inability to generate GAGs through recombinant genetic engineering strategies, combined with the inherent complexity that has been associated with their direct chemical synthesis, has stimulated the development of a variety of biomimetic synthetic approaches for the generation of carbohydrate-based macromolecules (Toshima, K. and Tatsuta, K. (1993) *Chem. Rev.* 93:1503; Roy, R. (1996) *Curr. Opin. Struct. Biol.* 6:692; and Roy, R. (1997) *Topics Curren. Chem.* 187:241).

Smaller oligosaccharide sequences may be responsible for the unique biological activities of the parent polysaccharides (Van Boeckel, C. A. A. et al. (1993) *Chem. Int. Ed. Engl.* 32:1671; Westerduin, P. et al. (1996) *Chem. Int. Ed. Engl.* 35:331; Petitou, M. et al. (1998), *Chem. Int. Ed.* 37:3009; Petitou, M. et al. (1999) *Nature* 398:417; Westman, J. et al. (1995) *Carbohydr. Chem.* 14:95; and Ornitz, D. M. et al. (1995) *Science* 268:432). While advantages of such an approach exist, an inherent limitation is the loss of spatially controlled organization of multiple target saccharide sequences. Indeed the observation of enhanced protein binding affinity derived from multivalent oligosaccharide ligands has been termed the "cluster glycoside effect" (Lee, Y. C. In *Synthetic Oligosaccharides: Indispensable Probes for the Life Sciences*, ACS Symposium Series 560, Washington, D.C. 1994, Chapter 1, p. 6; Dimick, S. M. et al. (1999) *J. Am. Chem. Soc.* 121:10286; and Suda, Y. et al. (2000) *Polym. Prepr.* (Am. Chem. Soc., Div. Polym. Chem.) 41(2):1624).

An alternative glycomimetic strategy has consisted of the design of synthetic polymers that contain a hydrocarbon backbone with biologically active pendent saccharides. Fundamental studies on the synthesis and properties of model "glycopolymers" have proven to be useful in the characterization of specific biomolecular recognition processes (Miyata, T. and Nakamae, K. (1997) *Trends Polym. Sci.* 5:198).

Optimization of glycopolymer properties has required the utilization of biomolecular architectures that exhibit low fluctuations both in polymer size and in composition. A large variety of "living"/controlled polymerization techniques have recently emerged for this purpose, including ring-opening polymerization of sugar-substituted N-carboxyanhydrides (Aoi, K. et al. (1992) *Macromolecules* 25:7073; and Aoi, K. et al. (1994) *Macromolecules* 27:875); ring-opening metathesis polymerization (ROMP) of sugar-derivatized norbornenes (Fraser, C. and Grubbs, R. H. (1995) *Macromolecules* 28:7248; Nomura, K. and Schrock, R. R. (1996) *Macromolecules* 29;540); cationic polymerization of saccharide-carrying vinyl ethers (Minoda, M. et al. (1995) *Macromol. Symp.* 99:169; Yamada, K. et al. (1997) *J. Polym. Sci. Part A: Polym. Chem.* 35:751; and Yamada, K. et al. (1999) *Macromolecules* 32:3553); anionic polymerization of styrene derivatives containing monosaccharide residues (Loykulnant, S. et al. (1998) *Macromolecules* 31:9121; and Loykulnant, S. and Kirao, A. (2000), *Macromolecules* 33:4757); nitroxide-mediated free-radical polymerization of sugar-carrying styryl (Ohno, K. et al. (1998) *Macromolecules* 31:1064; and Ohno, K. et al. (1998) *Macromol. Chem. Phys.* 199:2193); and acryloyl (Ohno, K. et al. (1999) *Macromol. Chem. Phys.* 200:1619); monomers, as well as Atom Transfer Radical Polymerization (ATRP) of carbohydrate-based methacrylates (Ohno, K. et al. (1998) *J. Polym. Sci., Part A: Polym. Chem.* 36:2473; Ejaz, M. et al. (2000) *Macromolecules* 33:2870; Bon, S. A. F. and Haddleton, D. M. (1999) *Polym. Prepr.* (Am. Chem. Soc., Div. Polym. Chem.) 40(2):248; and Marsh, A. et al. (1999) *J. Macromolecules* 32:8725). Nevertheless, due to the incompatibility of hydroxyl groups from the saccharide moieties with either initiators or controlling agents, all of these approaches require the use of protected monomers and the subsequent deprotection of polymer chains to generate the desired glycopolymers.

All publications referred to herein are incorporated herein in their entirety to the extent not inconsistent herewith.

SUMMARY

This invention provides a glycopolymer composition comprising glycopolymer molecules having a polymer backbone; a first pendent unit comprising a linking group connected to said polymer backbone and a saccharide moiety connected to said linking group; optionally a second pendent unit; a phenyl ring at a first end of the polymer backbone; and a cyanoxyl group at the second end of the polymer backbone.

These compounds are useful as, or as intermediates for making, bioactive glycopolymers for covalently or non-covalently binding to bioactive molecules. The molecules may be covalently bound to bioactive moieties through their end rings, or may bind to target bioactive molecules such as proteins, e.g. growth factors and cytokines, as well as viruses, cells and substrates, through their saccharide moieties, as is known to the art with respect to carbohydrate-mediated biomolecular recognition processes. The molecules of this invention or end products lacking the cyanoxyl group synthesized using these products as intermediates, are useful in protein separation, cell culture, and drug-delivery systems, as well as in targeting for treatment of wound healing and other pathological conditions.

The polymer backbone is preferably a straight chain, but may also be branched.

The first pendent unit comprises a hydrocarbyl linking group connected to the backbone. Preferably the linking group contains about 3 to about 9 atoms, most preferably carbon atoms. It is preferably $(CH_2)n$ where n is 3 to 9, and preferably is a straight chain, but may also be an unsaturated and/or branched chain, may comprise additional moieties attached to the chain, and the chain may comprise heteroatoms, so long as formation of the polymer via free radical polymerization is not interfered with by such heteroatoms, branching, and/or substituents. When the first pendent unit is made using an alkenyl-based glycomonomer, this helps lower the polydispersity index, thus it is preferred that an alkenyl-based glycomonomer be used.

The saccharide moieties are selected from the group consisting of monosaccharides, disaccharides, trisaccharides and oligosaccharides known to the art. Preferred saccharide moieties include N-acetyl-D-glucosamine, α- and β-N-acetyl-D-glucosamine-(1→4)-D-glucuronic acid, pyranosides, lactose, and polylactose. The saccharides may be fully or partially sulfated, or may be unsulfated, i.e. may have $SO_3$ moieties replacing OH moieties.

Preferably, the glycopolymer composition has a polydispersity index (molecular weight Mw/molecular number Mn) between about 1.1 and about 1.5.

The molecules of the glycopolymer composition preferably comprise between about 2 and about 1000 pendent saccharide moieties. When a second pendent is present, the sum of the number of saccharide moieties and second unit moieties is preferably no more than about 2000, more preferably no more than about 1000, and most preferably no more than about 100. The first and second units may be in cis- or trans- configuration with respect to each other. Consecutive first units may also be cis- or trans- to each other.

The second unit preferably comprises about 3 to about 9 atoms, and may comprise substituents, branches, and heteroatoms as does the linking group. It is preferably formed of an easily polymerizable hydrocarbyl monomer by copolymerization along with the first unit. Preferably the second unit is polymerized from acrylamide, acrylate, or alkenyl compounds, most preferably acrylamide. The molecules of this invention may comprise up to about 1000 of such second units. The second unit may function as a spacer, or may be derived from an easily-polymerizable monomer that promotes polymerization during the process of making the molecules of this invention.

The first and second units may be interspersed with each other in random order along the polymer backbone. As is known to the art, polymerization process parameters such as concentration of reactants, and temperature, will determine the statistical frequency and order of the first and second units.

The phenyl ring may comprise at least one substituent which, depending on the electronic and steric effects of any substituent present, as is known to the art, may be ortho, meta or para, to the position at which the ring attaches to the polymer backbone. Ring substituents can be hydrocarbyl, e.g. methoxy, alcohol, ether, amine, polyamine, sulfate, phosphate, nitrate, nitrite, halogen selected from the group consisting of chlorine, bromine and iodine, salts of the foregoing, and other substituents which do not interfere with formation of the polymer via free radical polymerization. Preferably the substituent is a para substituent, and preferably is chloro. In the process of making the compounds of this invention, the phenyl ring is derived from a corresponding diazonium salt.

The molecules of this invention may comprises hydrophobic and hydrophilic substituents as is known to the art. Preferably they are water soluble.

The molecules in solution are in equilibrium with free cyanoxyl radicals which may leave the terminal end of the polymer backbone, leaving it free to participate in further polymerization reactions.

In one embodiment, the molecules of this invention have the formula:

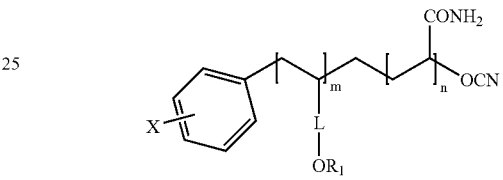

wherein X=H, Cl, $NO_2$ or $OCH_3$; L is a linker selected from the group of —$(CH_2)_p$— with p between 3 and about 9, or —$COO(CH_2)_2$—; $OR_1$ is selected from the group consisting of saccharide moieties; m is between 2 and about 1000; and n is between 0 and about 1000, wherein individual portions of the molecule designated by m and n may be in any order.

This invention also provides free radical polymerization methods for making the molecules of this invention. The method preferably comprises providing a cyanoxyl radical of an arenediazonium salt; providing glycomonomers comprising terminal vinyl groups, and polymerizing the glycomonomers in the presence of said cyanoxyl radicals. The method may also include providing comonomers to form a second unit as described above, such as acrylamide molecules comprising vinyl groups. The method includes forming the glycomonomers comprising terminal vinyl groups by attaching them to alkenyl, acrylate or acylamide or other linking groups as described above. The cyanoxyl radicals may be made by contacting arenediazonium salts with cyanate anions. These reactions may be performed in aqueous or organic solution, and preferably are performed in aqueous solution, which has the advantage of not destroying functional groups as readily as organic solution.

The method is preferably performed at a temperature between about 50 and about 70 degrees C., and preferably, especially when acrylamide is used to provide the second unit, the glycomonomers used to form the first unit are provided at a ratio to the monomers used to form the second unit of about 1:4. These reaction conditions and ratio of monomers may vary, as will be appreciated by those skilled in the art, when it is desired to achieve a different density of saccharide moieties or other properties.

The term "hydrocarbyl" is used herein to refer generally to organic groups comprised of carbon chains to which hydrogen and optionally other elements are attached. $CH_2$ or CH groups and C atoms of the carbon chains of the hydrocarbyl may be replaced with one or more heteroatoms (i.e., non-carbon atoms). Suitable heteroatoms include but are not limited to O, S, P and N atoms. The term hydrocarbyl includes, but is not limited to alkyl, alkenyl, alkynyl, ether, polyether, thioether, ascorbate, aminoalkyl, hydroxylalkyl, thioalkyl, aryl and heterocyclic aryl groups, amino acid, polyalcohol, glycol, groups which have a mixture of saturated and unsaturated bonds, carbocyclic rings and combinations of such groups. The term also includes straight-chain, branched-chain and cyclic structures or combinations thereof. Hydrocarbyl groups are optionally substituted. Hydrocarbyl substitution includes substitution at one or more carbons in the group by moieties containing heteroatoms. Suitable substituents for hydrocarbyl groups include but are not limited to halogens, including chlorine, fluorine, bromine and iodine, OH, SH, NH, $NH_2$, COH, $CO_2H$, $OR_a$, $SR_a$, $NR_aR_b$, $CONR_aR_b$, where $R_a$ and $R_b$ independently are alkyl, unsaturated alkyl or aryl groups, sulfate, sulfite, phosphate, nitrate, carbonyl, and polyamine.

A "carbonyl compound" is any compound containing a carbonyl group (—C=O). The term "amine" refers to a primary, secondary, or tertiary amine group. A "polyamine" is a group that contains more than one amine group. A "sulfate" group is a salt of sulfuric acid. Sulfate groups include the group $(SO_4)^{2-}$ and sulfate radicals. "Phosphates" contain the group $PO_4^{3-}$. "Glycols" are groups that have two alcohol groups per molecule of the compound.

The term "alkyl" takes its usual meaning in the art and is intended to include straight-chain, branched and cycloalkyl groups. The term includes, but is not limited to, methyl, ethyl, n-propyl, isopropyl, n-butyl, sec-butyl, isobutyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propylbutyl. Alkyl groups are optionally substituted. Lower alkyl groups are $C_1-C_6$ alkyl and include among others methyl, ethyl, n-propyl, and isopropyl groups.

The term "cycloalkyl" refers to alkyl groups having a hydrocarbon ring, preferably to those having rings of 3 to 7 carbon atoms. Cycloalkyl groups include those with alkyl group substitution on the ring. Cycloalkyl groups can include straight-chain and branched-chain portions. Cycloalkyl groups include but are not limited to cyclopropyl, cyclobutyl, cyclopentyl, cyclohexyl, cycloheptyl, cyclooctyl, and cyclononyl. Cycloalkyl groups can optionally be substituted.

Aryl groups may be substituted with one, two or more simple substituents including, but not limited to, lower alkyl, e.g., methyl, ethyl, butyl; halo, e.g., chloro, bromo; nitro; sulfato; sulfonyloxy; carboxy; carbo-lower-alkoxy, e.g., carbomethoxy, carbethoxy; amino; mono- and di-lower-alkylamino, e.g., methylamino, ethylamino, dimethylamino, methylethylamino; amido; hydroxy; lower-alkoxy, e.g., methoxy, ethoxy; and lower-alkanoyloxy, e.g., acetoxy.

The term "unsaturated alkyl" group is used herein generally to include alkyl groups in which one or more carbon-carbon single bonds have been converted to carbon-carbon double or triple bonds. The term includes alkenyl and alkynyl groups in their most general sense. The term is intended to include groups having more than one double or triple bond, or combinations of double and triple bonds. Unsaturated alkyl groups include, without limitation, unsaturated straight-chain, branched or cycloalkyl groups. Unsaturated alkyl groups include without limitation: vinyl, allyl, propenyl, isopropenyl, butenyl, pentenyl, hexenyl, hexadienyl, heptenyl, cyclopropenyl, cyclobutenyl, cyclopentenyl, cyclopentadienyl, cyclohexenyl, cyclohexadienyl, 1-propenyl, 2-butenyl, 2-methyl-2-butenyl, ethynyl, propargyl, 3-methyl-1-pentynyl, and 2-heptynyl. Unsaturated alkyl groups can optionally be substituted.

Substitution of alkyl, cycloalkyl and unsaturated alkyl groups includes substitution at one or more carbons in the group by moieties containing heteroatoms. Suitable substituents for these groups include but are not limited to OH, SH, $NH_2$, COH, $CO_2H$, $OR_c$, $SR_c$, P, PO, $NR_cR_d$, $CONR_cR_d$, and halogens, particularly chlorines and bromines where $R_c$ and $R_d$, independently, are alkyl, unsaturated alkyl or aryl groups. Preferred alkyl and unsaturated alkyl groups are the lower alkyl, alkenyl or alkynyl groups having from 1 to about 3 carbon atoms.

The term "aryl" is used herein generally to refer to aromatic groups which have at least one ring having a conjugated pi electron system and includes without limitation carbocyclic aryl, aralkyl, heterocyclic aryl, biaryl groups and heterocyclic biaryl, all of which can be optionally substituted. Preferred aryl groups have one or two aromatic rings.

"Carbocyclic aryl" refers to aryl groups in which the aromatic ring atoms are all carbons and includes without limitation phenyl, biphenyl and napthalene groups.

"Aralkyl" refers to an alkyl group substituted with an aryl group. Suitable aralkyl groups include among others benzyl, phenethyl and picolyl, and may be optionally substituted. Aralkyl groups include those with heterocyclic and carbocyclic aromatic moieties.

"Heterocyclic aryl groups" refers to groups having at least one heterocyclic aromatic ring with from 1 to 3 heteroatoms in the ring, the remainder being carbon atoms. Suitable heteroatoms include without limitation oxygen, sulfur, and nitrogen. Heterocyclic aryl groups include among others furanyl, thienyl, pyridyl, pyrrolyl, N-alkyl pyrrolo, pyrimidyl, pyrazinyl, imidazolyl, benzofuranyl, quinolinyl, and indolyl, all optionally substituted.

"Heterocyclic biaryl" refers to heterocyclic aryls in which a phenyl group is substituted by a heterocyclic aryl group ortho, meta or para to the point of attachment of the phenyl ring to the decalin or cyclohexane. Heterocyclic biaryl includes among others groups which have a phenyl group substituted with a heterocyclic aromatic ring. The aromatic rings in the heterocyclic biaryl group can be optionally substituted.

"Biaryl" refers to carbocyclic aryl groups in which a phenyl group is substituted by a carbocyclic aryl group ortho, meta or para to the point of attachment of the phenyl ring to the decalin or cyclohexane. Biaryl groups include among others a first phenyl group substituted with a second phenyl ring ortho, meta or para to the point of attachment of the first phenyl ring to the decalin or cyclohexane structure. Para substitution is preferred. The aromatic rings in the biaryl group can be optionally substituted.

Aryl group substitution includes substitutions by non-aryl groups (excluding H) at one or more carbons or where possible at one or more heteroatoms in aromatic rings in the aryl group. Unsubstituted aryl, in contrast, refers to aryl groups in which the aromatic ring carbons are all substituted with H, e.g. unsubstituted phenyl (—$C_6H_5$), or naphthyl (—$C_{10}H_7$). Suitable substituents for aryl groups include among others, alkyl groups, unsaturated alkyl groups, halogens, OH, SH, $NH_2$, COH, $CO_2H$, $OR_e$, $SR_e$, $NR_eR_f$, $CONR_eR_f$, where $R_e$ and $R_f$ independently are alkyl, unsaturated alkyl or aryl groups. Preferred substituents are OH, SH, $OR_e$, and $SR_e$ where $R_e$ is a lower alkyl, i.e., an alkyl group having from 1 to about 3 carbon atoms. Other preferred substituents are halogens, more preferably chlorine or bromine, and lower alkyl and unsaturated lower alkyl groups having from 1 to about 3 carbon atoms. Substituents include bridging groups between aromatic rings in the aryl group, such as —$CO_2$—, —CO—, —O—, —S—, —P—, —NH—, —CH=CH— and —$(CH_2)_\rho$— where $\rho$ is an integer from 1 to about 5, and preferably —$CH_2$—. Examples of aryl groups having bridging substituents include phenylbenzoate. Substituents also include moieties, such as —$(CH_2)_\rho$—, —O—$(CH_2)_\rho$— or —OCO—$(CH_2)_\rho$—, where $\rho$ is an integer from about 2 to 7, as appropriate for the moiety, which bridge two ring atoms in a single aromatic ring as, for example, in a 1, 2, 3, 4-tetrahydronaphthalene group. Alkyl and unsaturated alkyl substituents of aryl groups can in turn optionally be substituted as described supra for substituted alkyl and unsaturated allyl groups.

The terms "alkoxy group" and "thioalkoxy group" (also known as mercaptide groups, the sulfur analog of alkoxy groups) take their generally accepted meaning. Alkoxy groups include but are not limited to methoxy, ethoxy, n-propoxy, isopropoxy, n-butoxy, sec-butoxy, isobutoxy, tert-butoxy, n-pentyloxy, neopentyloxy, 2-methylbutoxy, 1-methylbutoxy, 1-ethyl propoxy, 1,1-dimethylpropoxy, n-hexyloxy, 1-methylpentyloxy, 2-methylpentyloxy, 3-methylpentyloxy, 4-methylpentyloxy, 3,3-dimethylbutoxy, 2,2-dimethoxybutoxy, 1–1-dimethylbutoxy, 2-ethylbutoxy, 1-ethylbutoxy, 1,3-dimethylbutoxy, n-pentyloxy, 5-methylhexyloxy, 4-methylhexyloxy, 3-methylhexyloxy, 2-methylhexyloxy, 1-methylhexyloxy, 3-ethylpentyloxy, 2-ethylpentyloxy, 1-ethylpentyloxy, 4,4-dimethylpentyloxy, 3,3-dimethylpentyloxy, 2,2-dimethylpentyloxy, 1,1-dimethylpentyloxy, n-octyloxy, 6-methylheptyloxy, 5-methylheptyloxy, 4-methylheptyloxy, 3-methylheptyloxy, 2-methylheptyloxy, 1-methylheptyloxy, 1-ethylhexyloxy, 1-propylpentyloxy, 3-ethylhexyloxy, 5,5-dimethylhexyloxy, 4,4-dimethylhexyloxy, 2,2-diethylbutoxy, 3,3-diethylbutoxy, 1-methyl-1-propylbutoxy, ethoxymethyl, n-propoxymethyl, isopropoxymethyl, sec-butoxymethyl, isobutoxymethyl, (1-ethyl propoxy)methyl, (2-ethylbutoxy)methyl, (1-ethylbutoxy)methyl, (2-ethylpentyloxy)methyl, (3-ethylpentyloxy)methyl, 2-methoxyethyl, 1-methoxyethyl, 2-ethoxyethyl, 3-methoxypropyl, 2-methoxypropyl, 1-methoxypropyl, 2-ethoxypropyl, 3-(n-propoxy)propyl, 4-methoxybutyl, 2-methoxybutyl, 4-ethoxybutyl, 2-ethoxybutyl, 5-ethoxypentyl, and 6-ethoxyhexyl. Thioalkoxy groups include but are not limited to the sulfur analogs of the alkoxy groups specifically listed supra.

"Optional" or "optionally" means that the subsequently described event or circumstance may or may not occur, and that the description includes instances where said event or circumstance occurs and instances in which it does not. For example, "optionally substituted phenyl" means that the phenyl radical may or may not be substituted and that the description includes both unsubstituted phenyl radicals and phenyl radicals wherein there is substitution.

"Contacting" reaction components with each other refers to providing a medium and/or reaction chamber in which the reaction components are placed together so that they can react with each other. Preferably, the reaction components are suspended or dissolved in a carrier fluid which is a liquid medium. "Maintaining reaction components in contact" means keeping the components together in such a way that they can react with each other.

Saccharides include straight chain or cyclic saccharides, i.e., mono-, di- and poly-, straight chain and cyclic saccharides. They may have optional substituents that do not interfere with polymerization or binding to the target protein or other biolobically active component, such as the substituents set forth above for hydrocarbyls. Straight chain saccharides that are useful in this invention include but are not limited to those molecules with a chain of 5 or 6 carbon atoms with one or more —OH groups attached, and either an aldehyde or ketone group. Cyclic saccharides are saccharides that are in a ring form. Disaccharides are compounds wherein two monosaccharide groups are linked. Polysaccharides (also referred to as oligosaccharides) are compounds wherein more than two monosaccharide groups are linked.

Water soluble groups or hydrophilic groups includes groups that, when included as a substituent, imparts substantial solubility in water to the compound. Water soluble groups include, but are not limited to alcohols; polyalcohols; straight chain or cyclic saccharides; amines and polyamines; sulfate groups; phosphate groups; ascorbate groups; alkyl chains optionally substituted with —OH at any position; glycols, including polyethylene glycols, and polyethers.

The term "biologically active" means capable of effecting a change in a living organism or component thereof.

The cyanoxyl glycopolymers of this invention may be further modified to remove the cyanoxyl moiety for use in medical applications. Compositions for use in medical applications are are preferably hydrophilic and are highly pure or are purified to a highly pure state such that the they may be injected into a human patient. They may comprise or be modified to comprise water soluble groups or hydrophilic groups which when included as substituents, impart substantial solubility in water to the compound. Water soluble groups include, but are not limited to alcohols; polyalcohols; straight chain or cyclic saccharides; amines and polyamines; sulfate groups; phosphate groups; ascorbate groups; alkyl chains optionally substituted with —OH at any position; glycols, including polyethylene glycols, and polyethers comprising atoms available for forming hydrogen bonds in aqueous solutions.

The polymerizable linkers used to facilitate polymerization of the molecules of this invention may be ethylene, ethylene glycol, oxyethylene, methylene glycol, trimethylene glycol, vinylpyrrolidones, and derivatives thereof, all as is known to the art. Polyethylene glycol can be rendered monofunctionally activated by forming an alkylene ether group at one end. The alkylene ether group may be any suitable alkoxy radical having 1–6 carbon atoms, for example, methoxy, ethoxy, propoxy, 2-propoxy, butoxy, hexyloxy, and the like.

Preferably, the compositions of this invention are "non-immunogenic," i.e. produce no appreciable immunogenic or allergic reaction when injected or otherwise implanted into the body of a human subject.

The terms "cytokine" and "growth factor" are used to describe biologically active molecules and active peptides (which may be either naturally occurring or synthetic) which aid in healing or regrowth of normal tissue including growth factors and active peptides. Cytokines can incite local cells to produce new collagen or tissue, or they can attract cells to a site in need of correction. Cytokines include interferons (IFN), tumor necrosis factors (TNF), interleukins, and colony stimulating factors (CSFs). Growth factors include osteogenic factor extract (OFE), epidermal growth factor (EGF), transforming growth factor (TGF) alpha, TGF-beta. (including any combination of TGF-beta.s), TGF-B 1, TGF-B2, platelet derived growth factor (PDGF-AA, PDGF-AB, PDGF-BB), acidic fibroblast growth factor (FGF), basic FGF, connective tissue activating peptides (CTAP), beta.-thromboglobulin, insulin-like growth factors, erythropoietin (EPO), nerve growth factor (NGF), bone morphogenic protein (BMP), osteogenic factors, and the like. Glycopolymers made using the compositions of this invention bound to cytokines or growth factors may serve as effective controlled release drug delivery means. By varying the chemical linkage between the glycosaminoglycan and the synthetic polymer, it is possible to vary the effect with respect to the release of the cytokine or growth factor. For example, when an "ester" linkage is used, the linkage is more easily broken under physiological conditions, allowing for sustained release of the growth factor or cytokine from the matrix. However, when an "ether" linkage is used, the bonds are not easily broken and the cytokine or growth factor will remain in place for longer periods of time with its active sites exposed, providing a biological effect on the natural substrate for the active site of the protein. It is possible to include a mixture of conjugates with different linkages so as to obtain variations in the effect with respect to the release of the cytokine or growth factor, i.e., the sustained release effect can be modified to obtain the desired rate of release.

DETAILED DESCRIPTION

Figure 1:
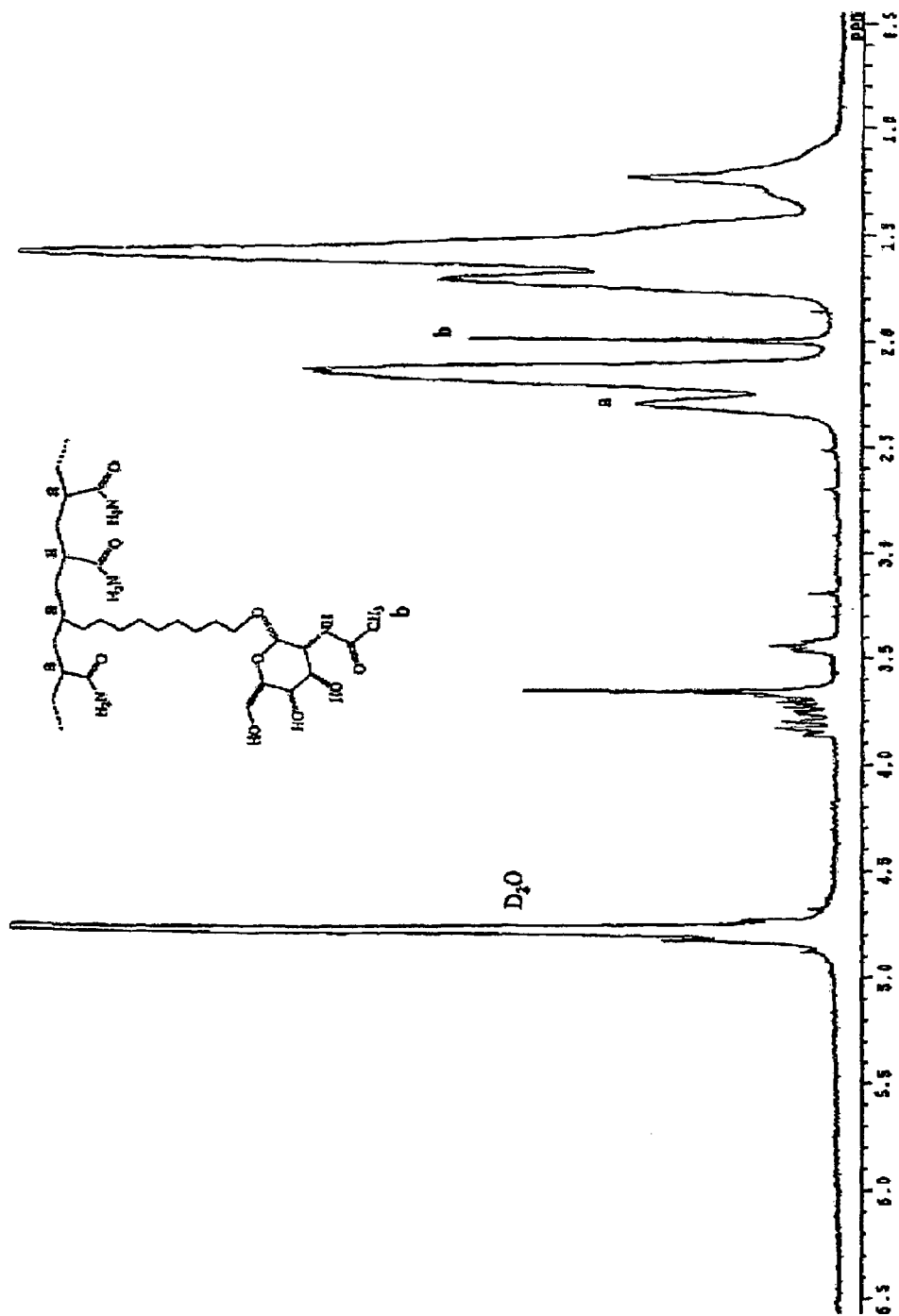
FIG. 1 shows an $^1$H NMR spectrum of a 5(C-9)/AM glycopolymer sample of this invention. The spectrum was recorded at room temperature with a Varian INOVA 400 spectrometer with a magnetic field strength of 400 MHz. The sample concentration was 10 mg/mL and $D_2O$ was used as the solvent and internal standard, 4.8 ppm.

This invention discloses synthesis of a series of model N-acetyl-D-glucosamine-carrying unprotected glycomonomers and their use in the synthesis of glycompolymers which serve as glycosaminoglycan-mimetic architectures. Some glycosaminoglycan-mimetic architectures are related to heparan sulfate. Well-characterized glycopolymers serve as useful model systems for investigating protein-carbohydrate interactions relevant to endothelial regeneration and angiogenesis. The design of biomaterials capable of promoting these physiological processes may have significant impact in the areas of wound repair and tissue regeneration, as well as other phenomena influenced by glycosaminoglycans. Tailored glycopolymers are contributing to the progress of glycotechnology, including the design of nonthrombogenic biomaterials that enhance tissue regeneration and wound healing responses. Tailored glycopolymers also provide model systems for investigating protein-carbohydrate interactions relevant to endothelial regeneration.

This invention broadens the family of vinyl monomers that are controllably polymerizable by using cyanoxyl-mediated free-radical polymerization. Both nonsulfated and sulfated alkene- as well as acrylate-derivatized monosaccharides are polymerizable using this methodology.

Cyanoxyl-mediated free-radical polymerization utilizes cyanoxyl persistent radicals as chain-growth moderators of the statistical copolymerization of acrylamide with either alkene- or acrylate-based glycomonomers. In association with a cyanoxyl-mediated polymerization strategy, acrylic monosaccharides are utilized to generate homo-glycopolymers with some degree of control. Cyanoxyl (.OC≡N)-mediated free-radical polymerization provides an effective and versatile method for engineering a diverse array of water-soluble glycopolymers with high saccharide contents and low polydispersity indexes preferably $1.1<M_w/M_n<1.6$.

Cyanoxyl-mediated free-radical polymerization can be conducted in aqueous solution, is tolerant of a broad range of functional groups (such as —OH, $NH_2$, —COOH, and others known to the art), yields low-polydispersity polymers, and is applicable to the synthesis of block and graft copolymers. Cyanoxyl-mediated copolymerization is an efficient approach for preparing glycopolymers with high monosaccharide contents and polymer compositions in close agreement with expected values.

The examples hereof demonstrate the synthesis of a series of mono- and disaccharide-containing glycopolymers by two different free radical processes. In the first methodology, cyanoxyl persistent radicals (.OC≡N) are effectively employed as moderators of the statistical copolymerization of acrylamide (AM) with either mono- or disaccharide-based ω-alkenyl glycomonomers. The statistical cyanoxyl-mediated copolymerization of acrylamide with either nonsulfated or sulfated alkene-derivatized unprotected glycomonomers is a practical and effective method for engineering a diverse array of glycopolymers with high saccharide contents and low polydispersity indexes. The results of this approach are compared to those obtained via the classical free-radical ammonium peroxodisulfate (APS)/N,N,N',N'-tetmethylethylenediamine (TMEDA) initiating system. The examples hereof illustrate the anticipated absence of control over copolymerization using the classical APS/TMEDA initiating system. It is not possible to synthesize a large variety of water-soluble glycopolymers with high carbohydrate contents and low polydispersity indexes ($1.1<M_w/M_n<1.5$) with classical free-radical polymerization such as using APS/TMEDA initiation.

Cyanoxyl persistent radicals impart control to the polymerization by scavenging growing radicals and forming dormant species that can reversibly undergo hemolytic bond cleavage, in a manner similar to that reported for nitroxyl-mediated processes. In the presence of cyanoxyl radicals that are unable to initiate polymerization, a low stationary concentration of macroradicals is maintained which prevents bimolecular irreversible termination from occurring to the extent observed in classical free-radical mechanisms. Further, the use of .OC≡N radicals generated at moderate temperatures (25–70° C.) avoids unintended thermal polymerization of monomers.

As a starting point for our synthetic studies, model vinyl-derivatived glycomonomers were synthesized from N-acetyl-D-glucosamine. However, a more efficient strategy was developed that yielded glycomonomers in a single step. Schemes 1 and 2 demonstrate the synthesis of heparan sulfate-related glycomonomers viz. monosaccharides (compound 2) and disaccharides (compound 4) which bear a glycosamine moiety at the reducing end containing a vinyl polymerizable double bond. The synthetic strategies are based on preparing the glucuronic acid-glucosamine (GluA-GluNAc) sequence utilizing different protecting and deprotecting strategies. Nonsulfated alkene-derivatized unprotected glycomonomers were directly synthesized from N-acetyl-D-glucosamine.

Scheme 8, and Table 3 demonstrate cyanoxyl (.OC≡N) persistent radicals used as moderators of the statistical copolymerization of AM with the synthesized glycomonomers. Example 8 demonstrates classical free-radical copolymerizations of glycomonomers and AM using APS/TMEDA. Example 9 demonstrates the synthesis of nonsulfated N-acetyl-D-glucosamine-carrying glycomonomer. Example 10 demonstrates the synthesis of nonsulfated

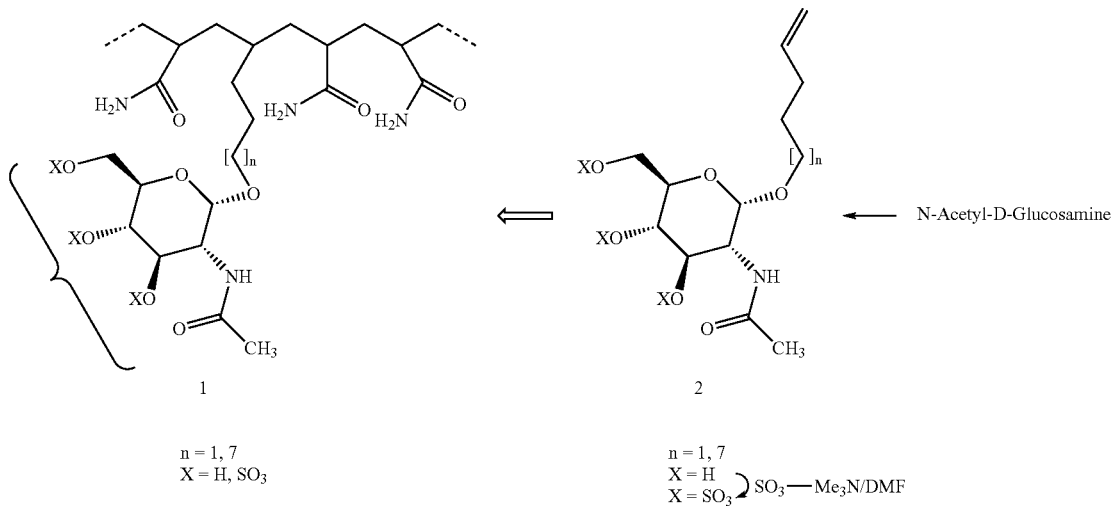

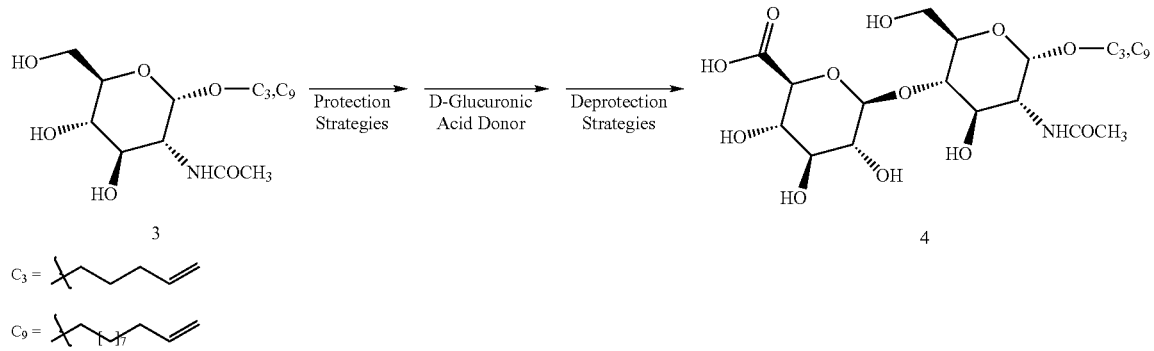

Example 1 and Scheme 3 demonstrate the synthesis of model glycomonomers from N-acetyl-D-glucosamine. Example 2 and Scheme 4 demonstrate the chemoselective sulfation of glycomonomer hydroxy groups. Example 3, Scheme 5, and Table 1 demonstrate cyanoxyl radical-mediated glycomonomer copolymerization. Example 4 and Table 2 demonstrate the preparation of acrylamide-based glycopolymers using the classical APS/TMEDA initiating system. Example 5 and Scheme 6 demonstrate the use of cyanoxyl radicals as moderators of the statistical copolymerization of acrylamide with the synthesized glycomonomers which provides a mechanism for controlling both polymer molar mass and architectural features based upon block structures. Example 6 and Scheme 7 demonstrate the synthesis of nonsulfated and sulfated glycopolymers. Example 7, lactose-based glycomonomer. Example 11 demonstrates the preparation of sulfated glycomonomers. Example 12 demonstrates the synthesis of nonsulfated GlcUA/GlcNAc bases glycomonomers. Example 13, Scheme 9, and Table 4 demonstrate cyanoxyl-mediated free-radical copolymerization of AM with alkene-derivatized unprotected glycomonomers. Example 14 and Table 5 demonstrate classical free-radical copolymerizations of glycomonomers and AM using APS/TMEDA. Example 15 and Scheme 10 demonstrate the synthesis of nonsulfated alkene-derivatized glycomonomers. Example 16 and Scheme 11 demonstrate the synthesis of nonsulfated acrylic monomers. Example 17 and Scheme 12 demonstrate the preparation of sulfated glycomonomers. Example 18 and Scheme 13 demonstrate the statistical polymerization of alkene-derivatized glycomonomers and acrylamide initiated by $ClC_6H_4N\equiv N^+BF_4^-$/NaOCN. Example 19 and Table 7 demonstrate homopolymerization of acrylic glycomonomers initiated by $ClC_6H_4N\equiv N^+BF_4^-$/NaOCN.

Regardless of the glycomonomer used (nonsulfated/sulfated, short/long spacer arm), it is remarkable that the carbohydrate contents as well as the molar masses increased with monomer conversion while the polydispersity indexes remained below 1.5. When an initial ratio of glycomonomer to AM of 1/4 was employed, a copolymer that displayed monosaccharide content in close agreement with that expected was obtained after 16 h of reaction. Weight proportions of sugar residues as high as 50% were thus reached. Nevertheless, a higher carbohydrate content in the resulting copolymer was associated with an increase in the polydispersity index. Thus, some loss of control over the copolymerization process sometimes occurs in the presence of increasing amounts of glycomonomer. This is probably due to the innate low chemical reactivity of the unactivated vinyl group in the saccharide monomer. It is also noteworthy that spacer-arm length of the glycomonomer influenced the polymerization behavior. Indeed, the amount of incorporated carbohydrate was increased with decreasing spacer-arm length.

Notably, saccharide contents as well as molar masses increased with monomer conversion while polydispersity indexes remained below 1.5. Regardless of the glycomonomer used (mono/disaccharide-based, nonsulfated/sulfated), an initial ratio GM/AM of 1/4, associated with a copolymerization time of 16 h, permitted access to a copolymer that displayed a saccharide content in close agreement with that expected. Samples exhibiting sugar compositions as high as 69 wt % were thus obtained. Nonetheless, copolymers with higher carbohydrate contents were associated with an increase in polydispersity indexes. This may be attributable to some loss of control over the copolymerization process in the presence of increasing amounts of ω-alkenyl glycomonomers, considering the innate low chemical reactivity of the unactivated vinyl group in these saccharide monomers.

Figure 2:
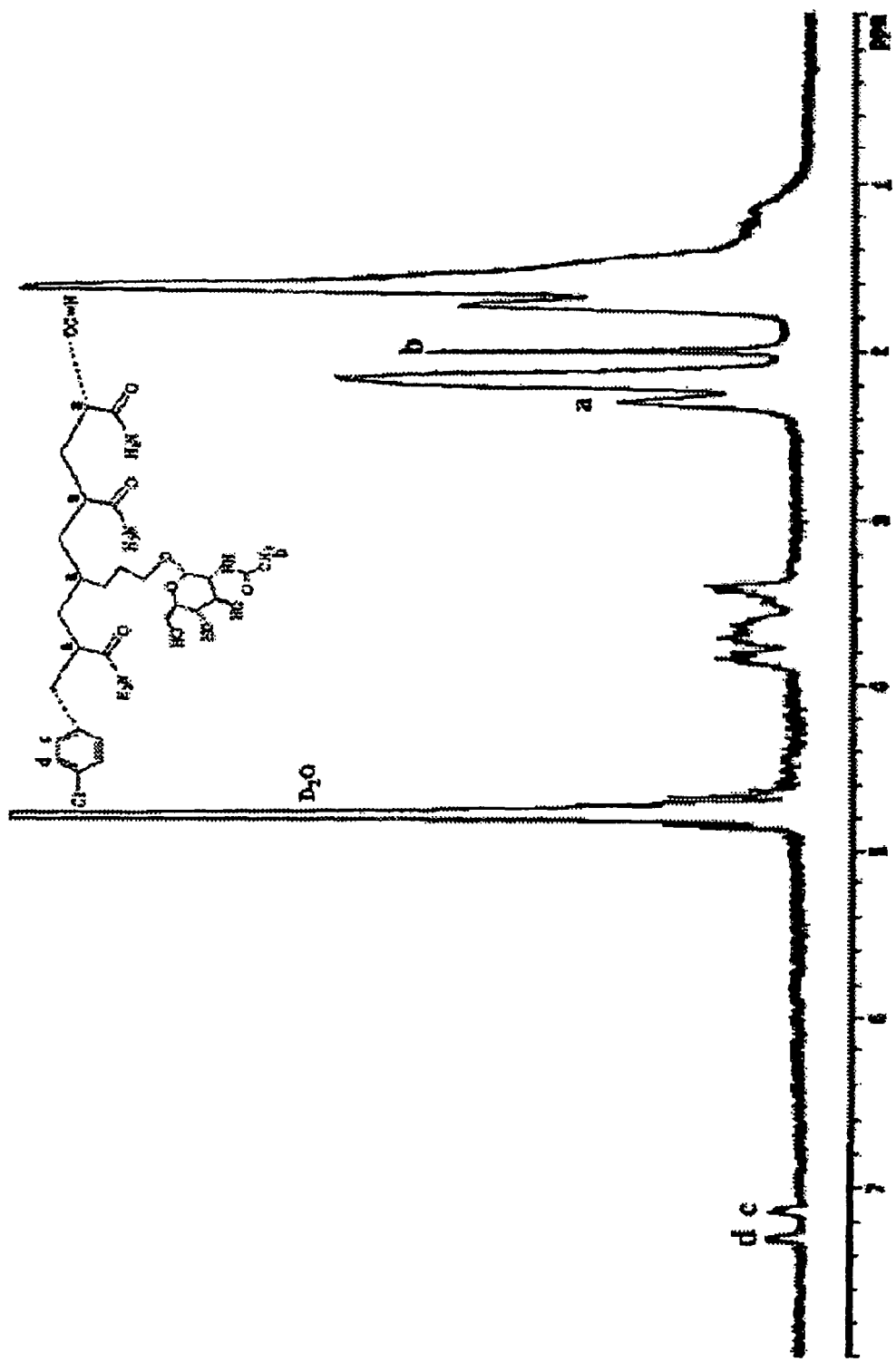
FIG. 2 shows an $^1$H NMR ($D_2O$) spectrum of a 17(C-3/AM glycopolymer sample of this invention (17(C-3)/AM=$^1$/$_{16}$ (mol) 17(C-3): 20 wt %, $M_{n,NMR}$=3700 g/mol, $M_{nSEC}$=4800 g/mol).
Figure 3:
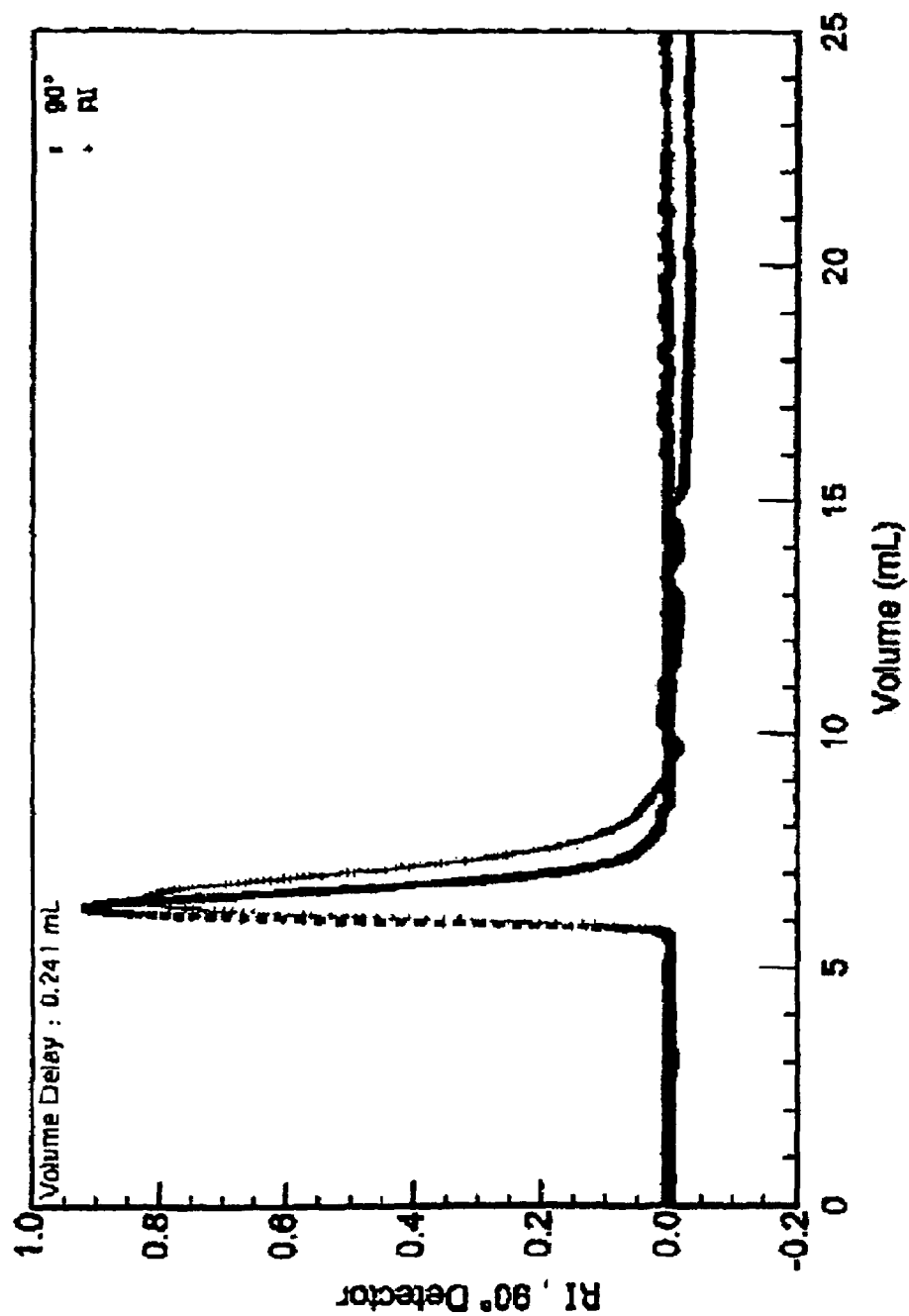
FIG. 3 shows a SEC/RI/LLS chromatogram of a 17(C-3)/AM glycopolymer sample ($M_n$=112,100 g/mol, $M_w/M_n$=1.20).

Cyanoxyl radicals were generated by an electron-transfer reaction between cyanate anions (.OC≡N), from a NaOCN aqueous solution, and p-chlorobenzene-diazonium salts ($ClC_6H_4N\equiv NBF_4^-$), that were previously prepared in situ through a diazotization reaction of p-chloroaniline in water (Example 18, Scheme 13). In addition to cyanoxyl persistent radicals, aryl-type active radicals were simultaneously produced, and only the latter species is capable of initiating chain growth. A large variety of water-soluble glycopolymers were generated by varying the nature of the ω-alkenyl glycomonomer (nonsulfated/sulfated, C-3/C-9 spacer arm), as well as the initial molar ratio of glycomonomer (GM) to acrylamide (AM) in the statistical cyanoxyl-mediated copolymerization of both comonomers (Table 6). Statistical copolymers were characterized by $^1$H NMR spectroscopy (see FIG. 2, as an example), as well as by size-exclusion chromatography (SEC) coupled with both refractive index (RI) and LLS detection systems (see FIG. 3, as an example). $^1$H NMR made it possible to verify the absence of residual comonomers, particularly glycomonomer, in the purified glycopolymers. The ratio of resonance signal intensities due to methyl protons from N-acetyl groups (2.0 ppm) and methine protons (2.1–2.4 ppm) from the hydrocarbon skeleton allowed determination of monosaccharide content. It is noteworthy that the spacer-arm length of ω-alkenyl glycomonomer influenced the copolymerization behavior. Indeed, the proportion of incorporated carbohydrate in the final copolymer increased with decreasing spacer-arm length from n-nonyl (C-9) to n-propyl (C-3). This suggests that C-3 spacer-armed glycomonomers have a higher reactivity than their C-9 homologues.

The degree of control over the macromolecular structure is significantly better with cyanoxyl-mediated free-radical polymerization than that observed by resorting to classical free-radical processes. Polydispersity indexes for all copolymers remained below 1.5, which defines a theoretical lower limit for a conventional free-radical mechanism. Moreover, regardless of the glycomonomer used and the initial GM/AM molar ratio, monosaccharide contents in the resulting glycopolymers as well as their molar masses increased with comonomer conversion. Yet, it should be stressed that contrary to a truly "living"/controlled radical polymerization, cyanoxyl-terminated samples of predetermined molar masses cannot be designed by ending the polymerization reaction at a certain conversion. Indeed, actual molar masses ($M_{nSEC}$ obtained from SEC/RI/LLS) were systematically much higher than theoretical values ($M_{nth}=M_0\times([M]_0/[I]_0)\times \pi$, where $M_0$ stands for the molar mass of a monomeric unit and $\pi$ for monomer conversion, assuming a complete initiator efficiency of f=1). We presume that a large proportion of the moderately reactive phenyl-type initiating radicals are lost in irreversible primary termination reactions at the initial stages of the polymerization process, thus decreasing initiator efficiency (f). Values as low as 0.1 were indeed estimated for this parameter by taking the ratio of theoretical to actual molar masses ($f=M_{n,th}/M_{n,SEC}$). On the other hand, it is also interesting to point out that the use of an initial GM/AM molar ratio of 1/4 enabled the design of a copolymer that exhibited a monosaccharide content in close agreement with that expected, after 16 h of reaction. Mass compositions of sugar residues as high as 50 wt % were thus reached. Nonetheless, a higher carbohydrate content in the resulting copolymers was associated with a broadening of the molar mass distributions ($M_w/M_n$). This is probably attributable to some loss of control over the copolymerization process in the presence of increasing amounts of ω-alkenyl glycomonomers, considering the innate low chemical reactivity of the unactivated vinyl group in these saccharide monomers.

The low level of polymerizability associated with alkene-derivatized monosaccharides in free-radical processes, and particularly in cyanoxyl-mediated polymerization, implies two major limitations. First, that the yield of copolymers with AM is low even after a reaction time of 16 h and second, that homopolymers cannot be derived from the polymerization of these glycomonomers, as confirmed by further investigation. Consequently, nonsulfated and sulfated acrylate-based glycomonomers were synthesized. As summarized in Table 7, cyanoxyl-mediated homopolymerization of these monosaccharides could be achieved with some degree of control. This is illustrated by the low polydispersity indexes ($1.13<M_w/M_n<1.56$) observed for nonsulfated and sulfated homo-glycopolymers. Samples of different molar masses were also prepared by varying either monomer conversion or the initial ratio of monomer to initiator concentrations ($[M]_0/[I]_0$). Acrylic glycomonomers were also copolymerized with AM to yield low-polydispersity (~1.5) statistical copolymers with saccharide contents as high as 75 wt %. Due to the much higher reactivity of acrylic monomers compared with that of their ω-alkenyl counterparts, higher conversions were reached within 4 h, or even 1.5 h in some instances (Table 2). However, polydispersity indexes of both nonsulfated and sulfated acrylic glycopolymers were generally higher than those obtained for alkene-derivatized homologues. Presumably, this arises from the non-negligible contribution of irreversible bimolecular termination reactions that characterizes free-radical polymerization of acrylates. The presence of cyanoxyl radicals as chain-growth moderators, nonetheless, makes it possible to minimize the extent of these side reactions.

All solvents and reagents were purchased from commercial sources and were used as received, unless otherwise noted. Deionized water with a resistivity of 18 MΩcm was used as solvent in all polymerization reactions.

All reactions were performed in flame-dried glassware under an atmosphere of dry argon. The reaction medium solutions were evaporated under reduced pressure with a rotary evaporator, and the residue was chromatographed on a silica gel (230–400 mesh) column. Analytical thin-layer chromatography (TLC) was performed on Whatman silica gel aluminum backed plates of 250 μm thickness on which spots were visualized with UV light or charring the plate before and/or after dipping in a $H_2SO_4$-EtOH mixture. Melting point (mp) measurements were performed with a Thomas Hoover melting point apparatus in open capillary tubes and were uncorrected. Mass spectra (MS/FAB) were obtained at an ionizing voltage of 70 eV. Optical rotations were determined with a Perkin Elmer-2 GIMC polarimeter. $^1H$ and $^{13}C$ NMR spectra were recorded at room temperature with a Varian INOVA 400 spectrometer (magnetic field strengths of 400 MHz and 100 MHz for $^1H$ and $^{13}C$ NMR analyses respectively). In all cases, the sample concentration was 10 mg/mL, and the appropriate deuterated solvent was used as internal standard. The size-exclusion chromatography (SEC) equipment comprised a Waters model 510 HPLC pump, a Waters Ultrahydrogel 250 column, and a Wyatt Technology Optilab 903 refractometer. The eluent consisted of a 0.1M $NaNO_3$ deionized water solution containing 0.05 wt % sodium azide at a flow rate of 0.7 mL/min. The actual molar masses of the glycopolymer samples were determined from the response of the DAWN F (Wyatt Technology) multiangle laser light-scattering (LLS) detector that was connected to the outlet of the SEC apparatus.

EXAMPLES

Example 1

Model glycomonomers were synthesized from N-acetyl-D-glucosamine. N-acetyl-D-glucosamine was treated with 4-penten-1-ol and ω-undecenol in the presence of 10-camphor sulphonic acid as catalyst. This reaction produced the α,β-anomeric mixture of the corresponding spacer-arm glycomonomer (Scheme 3). Anomers were successfully separated by column chromatography ($SiO_2$, $CHCl_3$/MeOH (9/1)) and were characterized by $^1H$ and $^{13}C$ NMR spectroscopy. Yields of the α- and β-anomers were 31% and 11%, respectively.

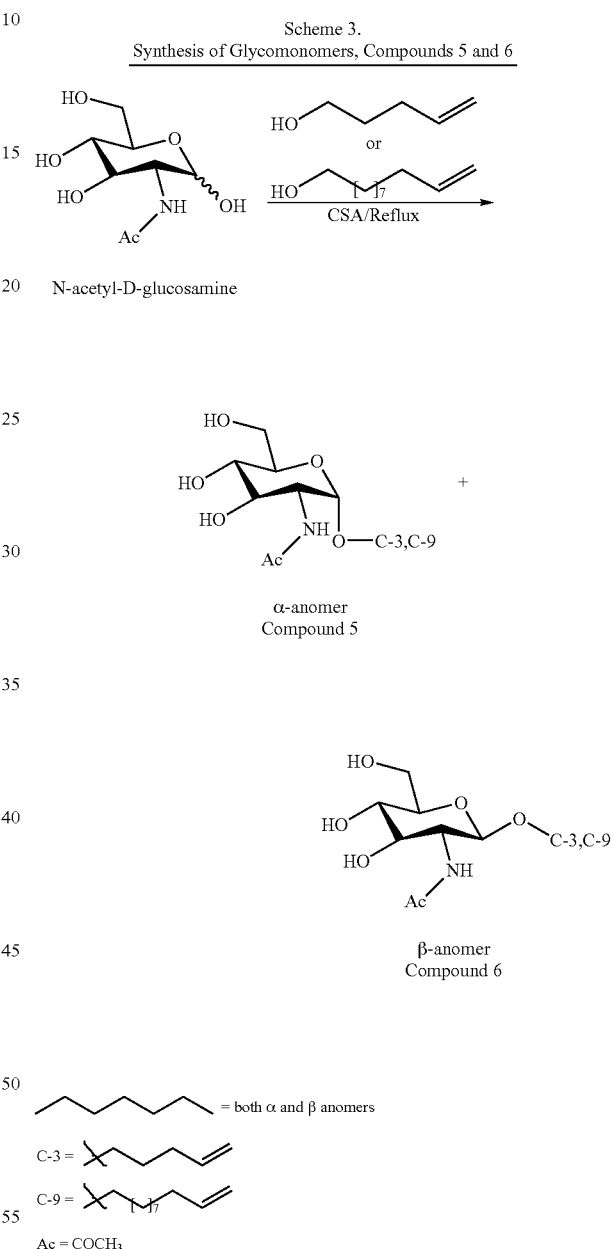

Example 2

Chemoselective sulfation of hydroxy groups with α-anomer was effected using $SO_3$ $NMe_3$ complex (scheme 4). The product was purified by anion-exchange and size exclusion chromatography and characterized by $^1H$ and $^{13}C$ NMR, as well as by mass spectral analysis.

Scheme 4.
Synthesis of Sulfated Glycomonomer, Compound 8

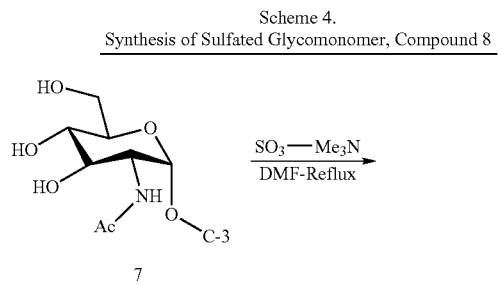

Example 3

Cyanoxyl radicals were generated in situ by an electron-transfer reaction between cyanate anions ($^-$OC≡N) and para-chloro-benzenediazonium cations (ClC$_6$H$_4$N≡N$^+$). Arenediazonium salts were prepared in water through a diazotization reaction of para-chloro-aniline (Scheme 5). The copolymerizations were performed at 50° C. or 70° C. using ClC$_6$H$_4$N≡N$^+$BF$_4^-$/NaOCN as the initiating system. Results are shown in Table 1. The statistical copolymers obtained were isolated by precipitation in a tenfold excess of methanol and characterized by $^1$H NMR spectroscopy (FIG. 1). The carbohydrate content of the copolymers was determined by using the ratio of the intensities of the resonance signals due to the methyl protons of N-acetyl groups from monosaccharide residues (2.0 ppm) and to the methine protons (between 2.1 and 2.4 ppm) of the main chain.

Regardless of the glycomonomer used (non sulfated/sulfated, short spacer-arm/long spacer-arm), when an initial ratio of glycomonomer to AM of 1/4 was employed, a copolymer that displayed a monosaccharide content in close agreement with that expected was obtained after 16 hours of reaction. Weight proportion of sugar residues as high as 50% were thus reached. Notably, an increase in the polymerization time (40 hours) did not significantly improve either the incorporation rate of the glycomonomer or the yield. However, an increase of the polymerization temperature from 50° C. to 70° C. did enhance the reactivity of the glycomonomer such that its incorporation rate was improved. It is of interest that spacer-arm length of the glycomonomer did influence polymerization behavior. Indeed, the amount of incorporated carbohydrate was increased with decreasing spacer-arm length. It is also noteworthy that the incorporation of the glycomonomer was improved at higher GM/AM ratios.

Scheme 5.
Copolymerization of AM with glycomonomers in the presence of cyanoxyl persistent radicals.

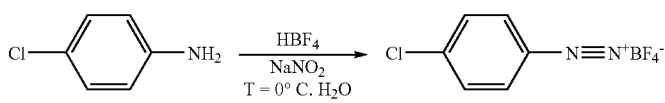

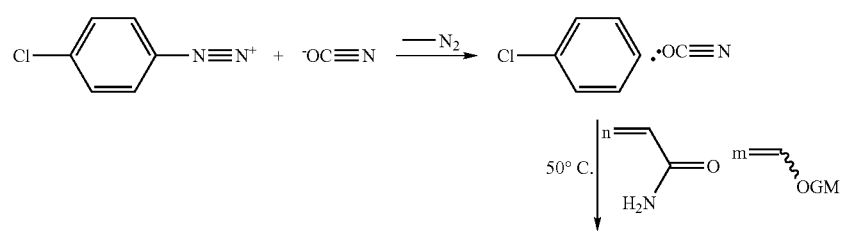

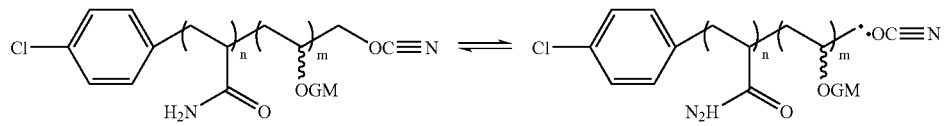

GM = sulfated or non sulfated sugar residue   ⁓ = C3 or C9 spacer-arm

TABLE 1

Experimental Conditions and Results of the Free-Radical Copolymerizations of AM with Miscellaneous Glycomonomers using ClC,H,N≡N⁺BF4⁻/NaOCN as initiating system

| Glycomonomer (GM) | Monomer Ratio GM/AM mol. | Time (h) | Yield (%) | Polymer Composition ¹H NMR (mol.) | Saccharide Content (wt %) |
|---|---|---|---|---|---|
| 5(C-3)[a] | 1/4 | 1.5 | 10 | 1/7 | 37.7 |
|  |  |  |  | 117 |  |
|  |  | 16 | 30 | 1/5 | 49.9 |
|  | 1/20 | 1.5 | 23 | 1/90 | 4.3 |
|  |  | 16 | 30 | 1/70 | 5.3 |
|  |  | 40 | 35 | 1/65 | 5.9 |
| 5(C-3)[b] | 1/20 | 1.5 | 20 | 1/70 | 5.4 |
|  |  | 16 | 26 | 1/50 | 6.9 |
| 5(C-9)[a] | 1/4 | 1.5 | 15 | 1/16 | 25.2 |
|  |  | 16 | 20 | 1/6 | 45.6 |
|  | 1/20 | 1.5 | 21 | 1/200 | 2.5 |
|  |  | 16 | 29 | 1/100 | 5.0 |
| 7[a] | 1/4 | 1.5 | 21 | 1/10 | 43.6 |
|  |  | 16 | 35 | 1/6 | 54.5 |
|  | 1/20 | 1.5 | 35 | 1/93 | 7.4 |
|  |  | 16 | 51 | 1/58 | 11.3 |

[a] $T = 50°$ C.;
[b] $T = 70°$ C.;
$[M]_0 = [GM]_0 + [AM]_0 = 1M$;
$[I]_0 = [ClC_6H_4N≡N^+BF_4^-]_0 = [NaOCN]_0 = 2 \times 10^{-2}$ M

Example 4

Classical free-radical copolymerizations of glycomonomers and AM were carried out using APS and TMEDA as the initiating system. TMEDA accelerates the homolytic scission of APS yielding sulfate ($SO_4^{2-}$), hemiTMEDA (($CH_3)_2NCH_2CH_2(CH_3)NCH_2.$), and hydroxyl (.OH) radical species. Copolymerization was performed in a dilute solution of water/methanol (1/1) [despite reports by Nishimura, S.-L; Matsuoka, K.; Kurita, K. (1990) Macromolecules 23:4182 and Nishimura, S.-L; Matsuoka, K.; Furuike, T.; Ishii, S.; Kurita, K. (1991) Macromolecules 24:4236 that 5(C-9) glycomonomer cannot undergo a copolymerization reaction in water due to its poor solubility]. The reaction medium was homogeneous and the polymerization proceeded efficiently at both room temperature and 50° C. Results of copolymerizations attempted with 5(C-3) or 5(C-9) glycomonomers are summarized in Table 2. After a defined reaction time, the medium was dialyzed against deionized water and freeze-dried to afford water-soluble statistical copolymers with yields up to 70%. Varying the initial GM/AM monomer ratio modified the sugar content in the macromolecules. Regardless of the conditions used in this series of experimental reactions, the glycomonomer incorporation rate was significantly lower than that obtained using cyanoxyl-mediated polymerization. Additionally, by increasing the temperature of the copolymerization from 25° C. to 50° C., the monosaccharide content was increased, though yield was decreased. This might be attributable to a higher loss of active centers at 50° C. However, this reduction in yield could be offset by increasing the initial monomer concentration.

TABLE 2

Experimental Conditions and Results of the Free-Radical Copolymerization of Compound 5(C-3) or Compound 5(C-9) Glycomonomer and AM in the presence of APS and TMEDA

| $[M]_0$ mol/L | $[I]_0$ (mol/L) | Time (h) | GM/AM (mol.) | Yield (%) | Polymer Composition ¹H NMR mol. | Saccharide Content (wt %) |
|---|---|---|---|---|---|---|
| 0.2[a] | 0.002 | 16 | 1/4 | 37 | 1/75 | 6.6 |
| 0.2[a] | 0.002 | 16 | 1/10 | 24 | 1/150 | 3.6 |
| 0.2[a] | 0.002 | 16 | 1/20 | 42 | 1/350 | 1.6 |
| 0.2[b] | 0.002 | 40 | 1/4 | 17 | 1/16 | 24.1 |
| 0.2[b] | 0.002 | 40 | 1/10 | 08 | 1/16 | 24.2 |
| 0.2[b] | 0.002 | 40 | 1/20 | 15 | 1/44 | 10.7 |
| 0.4[a] | 0.004 | 16 | 1/4 | 50 | 1/36 | 12.8 |
| 0.4[a] | 0.004 | 40 | 1/4 | 35 | 1/40 | 11.6 |
| 0.4[b] | 0.004 | 16 | 1/4 | 27 | 1/32 | 14.2 |
| 0.2[c] | 0.002 | 16 | 1/4 | 14 | 1/26 | 13.3 |
| 1[c] | 0.02 | 1.5 | 1/4 | 67 | 1/14 | 26.7 |
|  |  | 16 |  | 73 | 1/11 | 34.3 |
| 1[d] | 0.02 | 1.5 | 1/4 | 08 | 1/11 | 22.0 |
|  |  | 16 |  | 10 | 1/8 | 28.0 |

$[M]_0 = [GM]_0 + [AM]_0$; $[I]_0 = [APS]_0 = [TMEDA]_0$
[a] GM = 5(C-9), T = 25° C.;
[b] GM = 5(C-9), T = 50° C.;
[c] GM = 5(C-3), T = 25° C.
[d] GM = 5(C-3), T = 50° C.

Example 5

Synthesis of Nonsulfated and Sulfated Glycomonomers

N-acetyl-D-glucosamine, on treatment with 4-penten-1-ol or 10-undecen-1-ol in the presence of 10-camphorsulfonic acid (CSA) as catalyst, provided the α,β-anomeric mixture of the corresponding spacer arm containing glycomonomer (Scheme 6). Anomers 9 and 10 were successfully separated by column chromatography (5102, CHC131MeOH (911)) and were characterized by $^1H$ and $^{13}C$ NMR spectroscopy. Yields of α- and β-anomers were 31% and 11%, respectively.

Scheme 6.
Synthesis of Nonsulfated Glycomonomers, 9 and 10

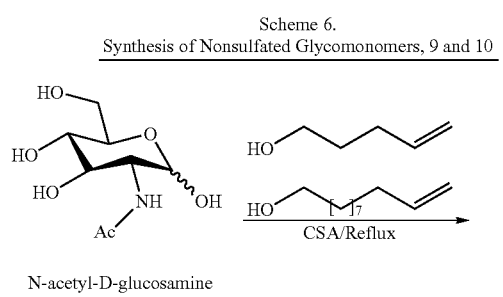

N-acetyl-D-glucosamine

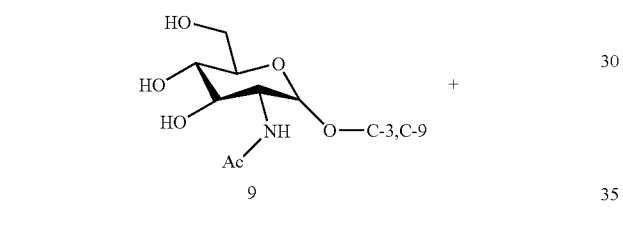

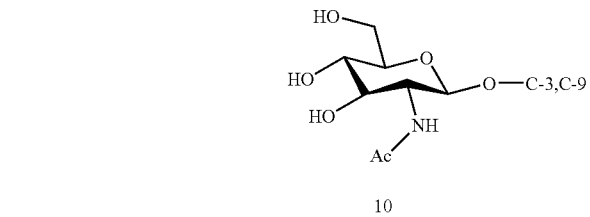

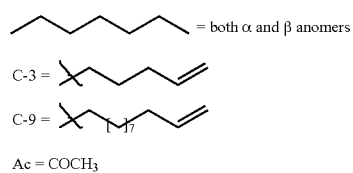

Ac = COCH$_3$

Example 6

Chemoselective sulfation of hydroxy groups on the α-anomer (9) was effected using the $SO_3$-$NMe_3$ complex (Scheme 7). The product (11) was purified by anion-exchange and size-exclusion chromatography and characterized by $^1H$ and $^{13}C$ NMR, as well as by mass spectral analysis.

Scheme 7.
Synthesis of Sulfated Glycomoners, 11

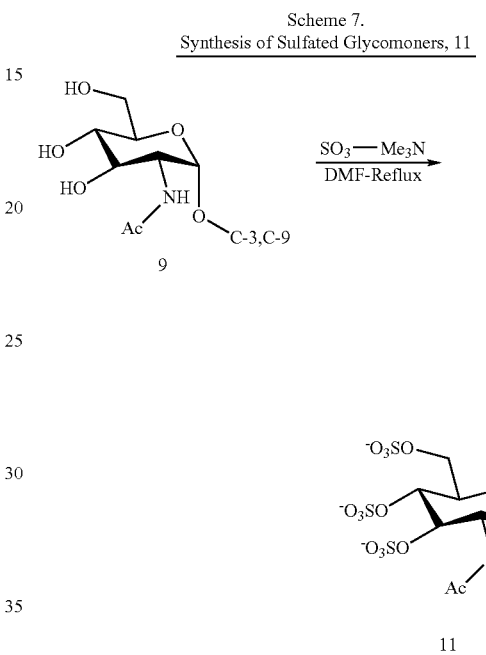

Example 7

Synthesis of Nonsulfated and Sulfated Glycopolymers

Cyanoxyl radicals were readily generated in situ by an electron-transfer reaction between cyanate anions ($^-OC\equiv N$) and p-chlorobenzenediazonium cations ($ClC_6H_4N\equiv N^+$). The arenediazonium salts were previously prepared in water through diazotization reaction of p-chloroaniline (Scheme 8). The results of copolymerizations performed at 50° C. using $ClC_6H_4N\equiv N^+BF_4^-$/NaOCN as the initiating system are shown in Table 3. The statistical copolymers obtained were isolated by precipitation in a 10-fold excess of methanol and characterized by $^1H$ NMR spectroscopy (see FIG. 1, as an example), as well as by size-exclusion chromatography (SEC) coupled with a refractive index (RI) detector and a multiangle laser light-scattering (LLS) detector. The monosaccharide content of the copolymers was determined by taking the ratio of the intensities of the resonance signals due to the methyl protons of N-acetyl groups from carbohydrate residues (2.0 ppm) and to the methine protons (between 2.1 and 2.4 ppm) of the main chain.

TABLE 3

Experimental Conditions and Results of Free-Radical Copolymerization of AM
with Miscellaneous Glycomonomers Using
$ClC_6H_4N{\equiv}N{+}BF_4{-}/NaOCN$ as Initiating System[a]

| glycomonomer (GM) | monomer ratio GM/AM (mol) | Time (h) | yield[b] (%) | polymer composition[c] (mol) | monosaccharide content (wt %) | $M_n$[d] (g/mol) | Mw/Mn SEC |
|---|---|---|---|---|---|---|---|
| 9(C-3) | 1/4 | 1.5 | 10 | 1/7 | 37.7 | 24,100 | 1.46 |
|  |  | 16 | 30 | 1/5 | 49.9 | 43,000 | 1.47 |
|  | 1/20 | 1.5 | 23 | 1/90 | 4.3 | 94,000 | 1.17 |
|  |  | 16 | 30 | 1/70 | 5.3 | 112,100 | 1.20 |
| 9(C-9) | 1/4 | 1.5 | 15 | 1/16 | 25.2 | 43,400 | 1.25 |
|  |  | 16 | 20 | 1/6 | 45.6 | 99,300 | 1.45 |
|  | 1/20 | 1.5 | 21 | 1/166 | 3.1 | 25,800 | 1.14 |
|  |  | 16 | 29 | 1/100 | 5.0 | 28,200 | 1.24 |
| 11(C-3) | 1/4 | 1.5 | 21 | 1/10 | 43.6 | 16,100 | 1.13 |
|  |  | 16 | 35 | 1/6 | 54.5 | 57,300 | 1.37 |
|  | 1/20 | 1.5 | 35 | 1/93 | 7.4 | 25,400 | 1.10 |
|  |  | 16 | 51 | 1/58 | 11.3 | 47,200 | 1.29 |
| 11(C-9) | 1/4 | 16 | 26 | 1/10 | 45.4 | 57,200 | 1.20 |
|  | 1/20 | 16 | 11 | 1/42 | 17.0 | 16,300 | 1.17 |

[a]$T = 50°$ C., $[M]_0 = [GM]_0 + [AM]_0 = 1M$, $[I]_0 = [ClC_6H_4N{\equiv}N^+BF_4^-]_0 = [NaOCN]_0 = 2 \times 10^{-2}$ mol/L.
[b]Total conversion of both comonomers as determined by gravimetry.
[c]Molar ratio of monosaccharide to acrylamide monomeric units in the resulting copolymer as determined by $^1$H NMR.
[d]$M_n$ obtained from SEC (eluent, water, column, Waters Ultrahydrogel 250) equipped with a LLS detector (Wyatt Technology).

Scheme 8.
Copolymerization of AM with glycomoners in the presence of cyanoxl persistent radicals

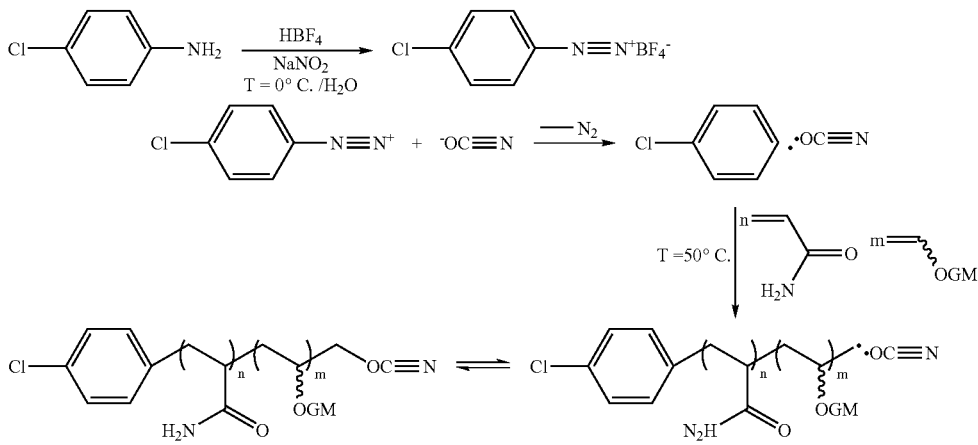

GM = sulfated or nonsulfated sugar residue ⁓⁓⁓ = C3 or C9 spacer-arm

Example 8

In a comparative analysis, classical free-radical copolymerizations of glycomonomers and AM were carried out using ammonium peroxodisulfate (APS) and N,N,N',N'-tetramethylethylene-diamine (TMEDA) as the initiating system. TMEDA accelerates the homolytic scission of APS yielding sulfate (SO4.$^-$), hemiTMEDA (($CH_3$)$_2$$NCH_2CH_2$($CH_3$)$NCH_2$.), and hydrox (.OH) radical species. However, we were able to obtain a copolymer by performing the copolymerization in a dilute solution of water/ThF (1/1). The reaction medium was homogeneous, and the polymerization proceeded efficiently at room temperature. Utilizing identical experimental conditions as those used for cyanoxyl-mediated processes ($[M]_o$=1 mol/L, $[I]_o$=2×10$^{-2}$ mol/L, GM(AM=1/4), the resulting glycopolymers exhibited lower monosaccharide contents (up to 30 wt %) and especially higher molar masses and polydispersity indexes (1.7–2.0). Moreover, increasing the polymerization time from 1.5 to 16 h increased the polydispersity index but otherwise had little effect on either monosaccharide content or molar mass.

Example 9

Synthesis of Nonsulfated N-acetyl-D-glucosamine-Carrying Glycomonomer

As a starting point for our synthetic studies, a nonsulfated alkene-derivatized unprotected monosaccharide (compound 12) was directly synthesized from N-acetyl-D-glucosamine. We resorted to the 10-camphorsulfonic acid (CSA)/reflux method as a facile means of yielding the desired C-3 spacer arm-containing glycomonomer. Thus, N-acetyl-D-glucosamine was refluxed at 110° C. for 9 h with a catalytic amount of CSA and a large excess of ω-pentenyl alcohol to provide a mixture of α- and β-anomers in an average 60–70% crude yield. The latter compounds were separated by silica gel column chromatography (eluent: CHCl$_3$/MeOH (9/1)) with a ratio (α/β) of 3/1, and were characterized by $^1$H and $^{13}$C NMR, as well as by mass spectrometry and polarimetry.

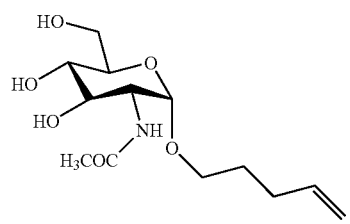

12

Example 10

Synthesis of Nonsulfated Lactose Based Glycomonomer

Lactose and ω-pentenyl alcohol were subjected to the aforementioned CSA/reflux methodology to yield a nonsulfated alkene-derivatized unprotected lactose (compound 13).

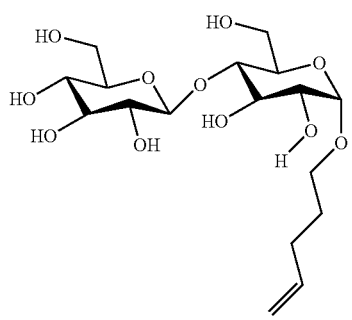

13

Example 11

Preparation of Sulfated Glycomonomers

Chemoselective sulfation of all hydroxyl groups on α-anomers, namely compounds 12 and 13, was achieved by treating them with SO$_3$—NMe$_3$ complex at 60° C. in DMF. This treatment actually resulted in crude mixtures of unreacted and sulfated derivatives. Hence, these mixtures were passed through a diethylaminoethyl (DEAE)-sephacel anion-exchange resin column, eluting first with a 10 mol/L sodium phosphate buffer (pH~7.0), whereby the unreacted nonsulfated compounds were removed. The sulfated homologues were then eluted with a 1 mol/L NaCl buffer (pH—7.0), and recovered as mixtures of their trisodium salts with an excess of NaCl. These eluates were finally passed through a Trisacryl size-exclusion resin column for isolation of the pure sulfated products (compounds 14 and 15) in 30–35% yield.

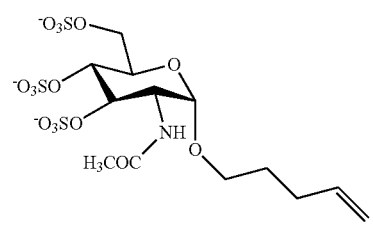

14

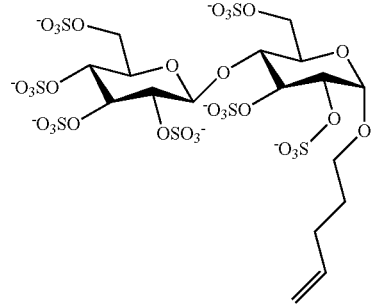

15

Example 12

Synthesis of Nonsulfated GlcUA/GlcNAc Based Glycomonomer

The target disaccharide sequence β-GlcUA-(1→4)-α-GlcNAc was derived from the glycosidation of the fully protected glucuronic acid (GlcUA) donor having an anomeric leaving group with the α-alkenyl N-acetyl-D glucosamine-containing (GlcNAc) acceptor which possesses an unprotected hydroxyl group at the 4-position. Successive protection/deprotection strategies were utilized to synthesize donor and acceptor molecules. All hydroxyl functionalities were deprotected in the resulting protected disaccharide and the carboxylic ester from the donor moiety was converted to the corresponding acid to afford the expected alkene-derivatized disaccharide (compound 16). This glycomonomer was thoroughly characterized by $^1$H NMR, $^{13}$C NMR and mass spectrometry.

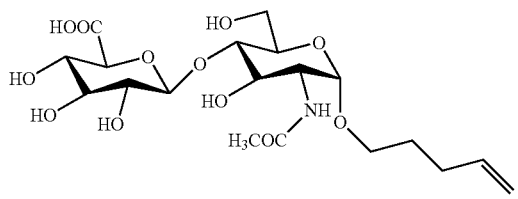

Example 13

Cyanoxyl radicals were readily generated by an electron-transfer reaction between cyanate anions (.OC≡N) from a NaOCN aqueous solution, and p-chlorobenzenediazonium salts (ClC$_6$H$_4$N≡N$^+$BF$_4^-$) that were previously prepared in situ through a diazotization reaction of p-chloroaniline in water. In addition to cyanoxyl persistent radicals, aryl-type active radicals were simultaneously produced, and only the latter species were able to initiate chain growth (Scheme 9). A variety of water-soluble glycopolymers were prepared by varying the nature of the α-alkenyl glycomonomer (nonsulfated/sulfated, mono-/disaccharide-based), as well as the initial molar ratio of glycomonomer (GM) to AM in the statistical copolymerization of both comonomers performed at 50° C. (Table 4). These statistical copolymers were isolated by precipitation in a 10-fold excess of methanol and characterized by $^1$H NMR spectroscopy, as well as by size-exclusion chromatography (SEC) coupled with both refractive index and laser light-scattering detectors. The absence of residual comonomers, and especially of glycomonomer in the purified glycopolymers, was checked by $^1$H NMR. The ratio of resonance signal intensity of methyl protons of N-acetyl groups from sugar moieties (2.0 ppm) to that of methine protons from the hydrocarbon skeleton (2.1–2.4 ppm) enabled the determination of saccharide content for glycopolymers containing N-acetyl-D-glucosamine residues. As to lactose-based samples, elemental analysis was used to assess their carbohydrate composition.

Scheme 9.
Cyanoxyl-Mediated Free-Radical Copolymerization of AM with Alkene-Derivatized Unprotected Glycomoners

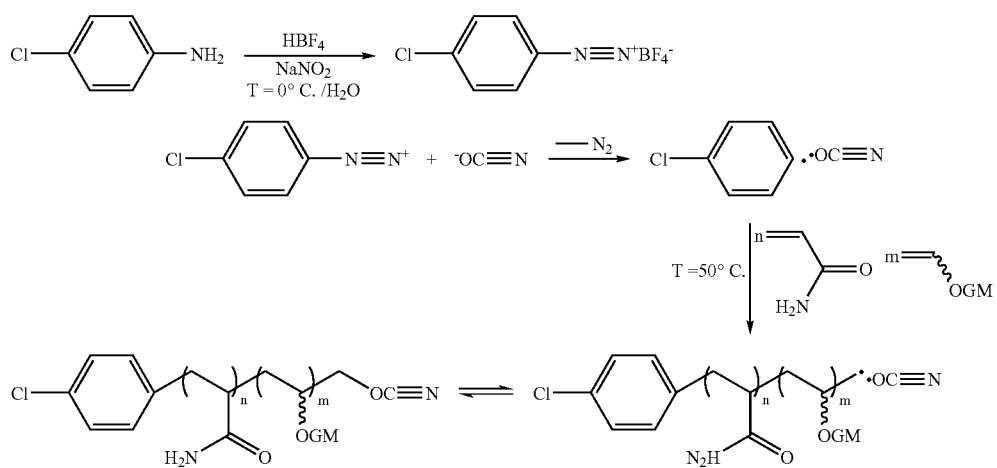

GM = sulfated or non sulfated saccharide residue          ∿∿∿ = C-3 spacer arm alkyl chain

TABLE 4

Statistical Free-Radical Copolymerization of AM with ω-Alkenyl Mono- or Disaccharide-Based Unprotected Glycomonomers Using ClC$_6$H$_4$N≡N$^+$BF4$^-$/NaOCN as Initiating System[a]

| GM | monomer ratio GM/AM (mol) | time (h) | yield[b] (%) | polymer composition GM/AM (mol) | saccharide content (wt %) | $M_n$ (g/mol) | $M_w/M_n$ SEC |
|---|---|---|---|---|---|---|---|
| 1 | 1/4  | 1.5 | 10 | 1/7  | 38 | 24,100  | 1.46 |
| 1 | 1/4  | 16  | 30 | 1/5  | 50 | 43,000  | 1.47 |
| 1 | 1/20 | 1.5 | 23 | 1/90 | 04 | 94,000  | 1.17 |
| 1 | 1/20 | 16  | 30 | 1/70 | 05 | 112,100 | 1.2  |
| 2 | 1/4  | 1.5 | 21 | 1/10 | 44 | 16,100  | 1.13 |
| 2 | 1/4  | 16  | 35 | 1/6  | 55 | 57,300  | 1.37 |
| 2 | 1/20 | 1.5 | 35 | 1/93 | 07 | 25,400  | 1.10 |
| 2 | 1/20 | 16  | 51 | 1/58 | 11 | 47,200  | 1.29 |
| 3 | 1/20 | 16  | 15 | 1/30 | 16 | 28,800  | 1.31 |

TABLE 4-continued

Statistical Free-Radical Copolymerization of AM with
ω-Alkenyl Mono- or Disaccharide-Based Unprotected
Glycomonomers Using $ClC_6H_4N{\equiv}N^+BF_4^-$/NaOCN as
Initiating System[a]

| GM | monomer ratio GM/AM (mol) | time (h) | yield[b] (%) | polymer composition GM/AM (mol) | saccharide content (wt %) | $M_n$ (g/mol) | $M_w/M_n$ SEC |
|---|---|---|---|---|---|---|---|
| 4 | 1/4 | 16 | 30 | 1/6 | 69 | 38,000 | 1.50 |
| 5 | 1/20 | 16 | 15 | 1/27 | 20 | 9,200 | 1.21 |

[a]T = 50° C., $[GM]_0 + [AM]_0$ = 1 mol/L, $[I]_0 = [ClC_6H_4N{\equiv}N^+BF_4^-]_0 = [NaOCN]_0$ = 0.02 mol/L.
[b]Total conversion of comonomers as determined by gravimetry.

Example 14

In a comparative study, classical free-radical copolymerizations of glycomonomers and AM were performed by using APS/TMEDA as the initiating system. TMEDA actually accelerates the homolytic scission of APS yielding sulfate ($SO_4^{2-}$), hemiTMEDA (($CH_3)_2NCH_2CH_2(CH_3)NCH_2$.), and hydroxyl (.OH) radical species. The reaction medium was homogeneous and the polymerization proceeded smoothly at room temperature (Table 5.) Utilizing otherwise identical experimental conditions as those used for cyanoxyl-mediated processes ($[M]_0$=1 mol/L, $[I]^0$=2× $10^{-2}$ mmol/L), the resulting glycopolymers exhibited lower saccharide contents (maximum: 43 wt %) and especially higher molar masses and polydispersity indexes (1.6–2.0). Moreover, increasing the polymerization time from 1.5 to 16 h increased the polydispersity index, but otherwise had little influence on either saccharide content or molar mass.

tography with a ratio (α/β) of 3/1 for both cases. The yield was improved by varying the temperature and reaction time. The α- and β-anomeric configurations of the separated products were determined from $^1$H NMR data, namely $J_{1,2}$ coupling constants of 3.6 Hz and 8.0 Hz, respectively. To a mixture of N-acetyl-D-glucosamine (10 g) and either 4-penten-1-ol or 10-undecen-1-ol (large excess, ~50–75 mL) was added a catalytic amount of 10-camphorsulphonic acid (CSA) (~400 mg) and the mixture was refluxed at 110° C. for 9 h. The reaction mixture was then cooled, neutralized with triethylamine, and the excess of alcohol was removed under vacuum. Moreover, the rest of the solid mass was rinsed with hot petroleum ether to remove the rest of ω-alkenyl alcohol. The residue was purified by column chromatography using a chloroform/methanol (97/3) mixture to afford the expected α-and β-anomers. (Scheme 10, 17(C-3) or 17(C-9), and 18(C-3) or 13(C-9), respectively).

TABLE 5

Statistical Free-Radical Copolymerization of AM with
ω-Alkenyl Mono- or Disaccharide-Based Unprotected
Glycomonomers Using APS/TMEDA as Initiating System[a]

| GM | monomer ratio GM/AM (mol) | time (h) | yield[b] (%) | polymer composition GM/AM (mol) | saccharide content (wt %) | $M_n$ (g/mol) | $M_w/M_n$ SEC |
|---|---|---|---|---|---|---|---|
| 1 | 1/4 | 1.5 | 67 | 1/14 | 22 | 133,000 | 1.63 |
| 1 | 1/4 | 16 | 73 | 1/11 | 28 | 146,000 | 1.73 |
| 3 | 1/4 | 16 | 83 | 1/10 | 38 | 140,000 | 1.78 |
| 3 | 1/20 | 16 | 80 | 1/48 | 11 | 156,000 | 2.08 |
| 4 | 1/4 | 16 | 50 | 1/18 | 43 | 70,500 | 1.59 |
| 4 | 1/20 | 16 | 70 | 1/60 | 18 | 80,000 | 1.89 |
| 5 | 1/20 | 16 | 69 | 1/20 | 25 | 54,400 | 1.62 |
| 5 | 1/20 | 16 | 66 | 1/75 | 08 | 44,500 | 1.60 |

[a]T = 25° C., $[M]_0 = [GM]_0 + [AM]_0$ = 1 mol/L, $[I]_0 = [APS]_0 = [TMEDA]_0$ = 0.02 mol/L.
[b]Total conversion of comonomers as determined by gravimetry.

Example 15

Synthesis of Nonsulfated Alkene-Derivatized Glycomonomers

Hence, N-acetyl-D-glucosamine was refluxed with a catalytic amount of CSA and a large excess of either α-pentenyl or ω-undecenyl alcohol to provide a mixture of α- and β-anomers (Scheme 10, 17(C-3) or 17(C-9), and 18(C-3) or 18(C-9), respectively) in an average 60–70% crude yield. The latter compounds were separated by column chroman-Pentenyl 2-Acetamido-2-deoxy-α-D-glucopyranoside, 17(C-3)

Yield: 46%. mp: 146–148° C. $[\alpha]_D^{20}$=+142.2° (c 1.3, MeOH). $^1$H NMR (CDCl$_3$+5% CD$_3$OD), $\delta_{ppm}$: 1.68 (m, 2H), 2.02 (s, 3H, NHCOCH$_3$), 2.12 (m, 2H), 3.41 (dt, IH, J =6.4 and 10 Hz), 3.68 (m, 4H), 3.78 (d, 1H, J=3.2 and 12.4 Hz), 4.00 (dd, IH, J=3.2 and 12.4 Hz), 4.02 (m, 1H), 4.77 (d, IH, $J_{1,2}$=3.6 Hz, H-1), 5.01 (m, 2H, CH$_2$═), 5.80 (m, 1H, CH═), 6.61 (d, 1H, J=8.8 Hz, NHCOCH$_3$). $^{13}$C NMR (CDCl$_3$+5% CD$_3$OD), $\delta_{ppm}$: 22.9, 28.4, 30.2, 53.6, 61.2, 67.2, 70.1, 71.6, 72.4, 97.3, 114.9, 137.9, 171.7. MS/FAB, m/z: 289 (M$^+$).

n-Undecenyl 2-Acetamido-2-deoxy-α-D-glucopyranoside, 17(C-9)

Yield: 50%. mp: 152–154° C. $[\alpha]_D^{20}$ =−9.0° (c 0.2; MeOH). $^1$HNMR (CDCl$_3$+5% CD$_3$OD), $\delta_{ppm}$: 1.34 (m, 9H), 1.54 (m, 2H), 2.02 (m and s, 5H), 3.33 (m, 1H), 3.68 (m, 4H), 3.77 (br d, 1H, J=9.6 Hz), 3.92 (br d, 1H, J=9.6 Hz), 4.06 (m, IH), 4.78 (d, 1H, J$_{1,2}$=3.6 Hz, H-1); 4.95 (m, 2H, CH$_2$=), 5.80 (m, 1-H, CH=), 6.43 (d, 1H, J=8.8 Hz, NHCOCH$_3$). $^{13}$C NMR (CDCl$_3$+5% CD$_3$OD), $\delta_{ppm}$: 23.3, 26.1, 28.9, 29.1, 29.3, 29.4, 29.5, 29.6, 33.8, 53.7, 61.2, 68.0, 69.9, 71.6, 72.8, 97.4, 114.1, 139.1, 171.7. MS/FAB, m/z: 373 (M$^+$).

n-Pentenyl 2-Acetamido-2-deoxy β-D-glucopyranoside, 18(C-3)

Yield: 15%. Detailed characterization data have been previously reported by Nishimura, S. I.; Matsuoka, K.; Furuike, T.; Ishii, S.; Kurita, K. Macromolecules 1991, 24, 4236.

n-Undecenyl 2-Acetamido-2-deoxy-β-D-glucopyranoside, 18(C-9)

Yield: 16%. mp: 175–177° C. $[\alpha]_D^{20}$=−7.0° (c 0.23, MeOH). $^1$H NMR (CDCl$_3$+5% CD$_3$OD), $\delta_{ppm}$: 1.32 (m, 9H), 1.54 (m, 2H), 2.01 (m and s, 5H), 3.32 (M, 1H), 3.47 (M, 2H), 3.54 (m, 2H), 3.84 (m, 3H), 4.47 (d, 1H, J$_{1,2}$=8.0Hz, H-1), 4.96 (m, 2H, CH$_2$=), 5.81 (m, 1H, CH=). MS/FAB, m/z: 373 (M$^+$).

Scheme 10.
Synthesis of Nonsulfated Alkene-Derivatized Glycomoners

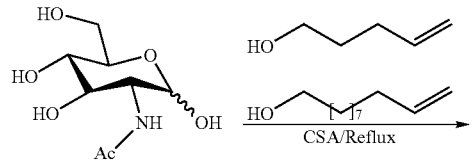

N-acetyl-D-glucosamine

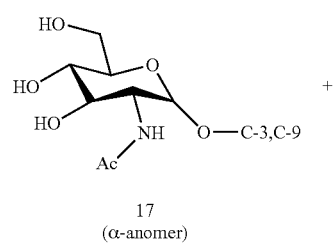

17
(α-anomer)

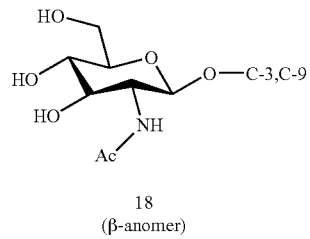

18
(β-anomer)

C-3 = 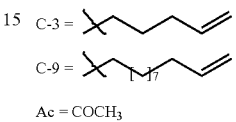

C-9 =

Ac = COCH$_3$

Example 16

Synthesis of Nonsulfated Acrylic Glycomonomers

Acrylic monomer 19 was directly synthesized from N-acetyl-n-Glucosamine as depicted in Scheme 11. Treatment of this carbohydrate with 2-hydroxyethyl acrylate in the presence of phosphomolybdic acid as catalyst and 1-chloro-2,4-dinitrobenzene as polymerization inhibitor yielded a crude α,β-anomeric mixture (compounds 19 and 20, respectively) in an overall yield close to 50%. Column chromatography allowed both anomers to be separated with a ratio (α/β) of 3.5/1. They were characterized by $^1$H and $^{13}$C NMR, as well as by mass spectrometry. A mixture of N-acetyl-D-glucosamine (10 g, 45 mmol), 2-hydroxyethyl acrylate (52 g, 450 mmol), chlorobenzene (10 g, 90 mmol), phosphomolybdic acid (0.82 g, 0.45 mmol) and 1-chloro-2,4-dinitrochlorobenzene (1 g, 4.5 mmol) was heated to 110° C. The reaction was monitored by TLC; after 5 h, the reaction mixture was cooled and then neutralized with a saturated NaHCO$_3$ aqueous solution. The crude product obtained was purified by column chromatography with a chloroform/methanol (96/4) mixture whereby the α-anomer (Scheme 11, compound 19) was recovered as a viscous oil and the β-anomer (Scheme 11, compound 20) was isolated as a white powder.

2S-(4,5-dihydroxy-6-hydroxymethyl-3-methylcarboxamidotetrahydro-2H-2-pyranyloxy)ethyl acrylate, 19

Yield: 37%, $[\alpha]_D^{20}$=32.5° (c 2, CHCL$_3$). $^1$H NMR (CDCl$_3$), $\delta_{ppm}$: 1.88 (s, 3H. NHCOCH$_3$ ), 3.38–3.66 (m, 7H), 3.81 (m, 1H), 4.17 (m, 3H),4.70 (d, 1H, J$_{1,2}$=3.5 Hz, H-1), 5.79 (d, 1H, J=10.5 Hz, CH$_2$=), 6.05 (dd, 1H, J=10.5 and 17.2 Hz, CH=), 6.29 (d, 1H, J=17.2 Hz, CH$_2$=). $^{13}$C NMR (CDCl$_3$), $\delta_{ppm}$: 22.5, 53.3, 61.2, 63.1, 65.7, 68.6, 70.3, 71.9, 97.5, 127.7, 131.6, 167.0, 172.0. MS/FAB, m/z: 320 (M$^+$+H$^+$).

2R-(4,5-dihydroxy-6-hydroxymethyl-3-methyl carboxamidotetrahydro-2H-2-pranyloxy)ethyl acrylate 20.

Yield: 11%. mp: 138–140° C. $[\alpha]_D^{20}$=+24.5° (c 2, CHCl$_3$). $^1$H NMR (CDCL$_3$), $\delta_{ppm}$: 1.89 (s, 3H, NHCOCH$_3$), 3.28–3.48 (m, 5H), 3.35 (m, 1H), 3.44 (m, 1H), 3.64–3.78

(m, 3H), 3.91 (m,1H), 4.17 (m, 1H), 4.28 (m, 1H), 4.43 (d, 1H, $J_{1,2}$=7.9 Hz, H-1), 5.80 (d, 1H, J=10.4 Hz, $CH_2$=), 6.05 (dd, 1H, J=10.4 and 17.5 Hz, CH=), 6.36 (d, 1H, J=17.5 Hz, $CH_2$=). $^{13}C$ NMR ($CDCl_3$), $\delta_{ppm}$: 22.7, 56.2, 61.5, 63.1, 66.3, 70.6, 74.7, 75.8, 100.3, 127.8, 131.5, 166.2, 172.6. MS/FAB, m/z: 320 ($M^+ + H^+$).

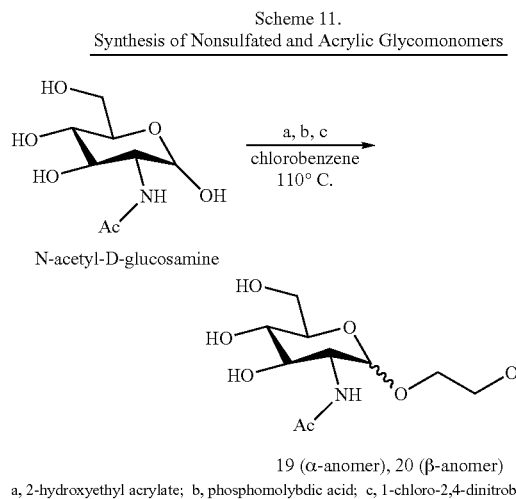

Scheme 11.
Synthesis of Nonsulfated and Acrylic Glycomonomers

N-acetyl-D-glucosamine 19 (α-anomer), 20 (β-anomer)
a, 2-hydroxyethyl acrylate; b, phosphomolybdic acid; c, 1-chloro-2,4-dinitrobenzene

Example 17

Preparation of Sulfated Glycomonomers

Chemoselective sulfation of all hydroxyl groups on α-anomers, namely 17(C-3), 17(C-9), and 19, was achieved by treating these monosaccharides with $SO_3$—$NMe_3$ complex at 60° C. As expected, a relative downfield shift in the $^1H$ NMR spectra of the sulfated glycomonomers (compounds 21(C-3), 21(C-9), and 22 was observed when compared with their nonsulfated homologues. Under argon atmosphere, the appropriate amount of sulfur trioxide-trimethylamine ($SO_3$—$NMe_3$) complex (4 eq. for each hydroxyl group) was added to a nonsulfated glycomonomer in DMF, and the mixture was stirred at 60° C. for 12 h. The reaction medium was then cooled to 0° C., and a saturated $NaHCO_3$ aqueous solution was added. The crude mixture was stirred for 1 h and concentrated to a smaller volume that was passed through a diethylaminoethyl (DEAE)-sephacel anion-exchange resin column. It was first eluted with a 10 mM sodium phosphate buffer (pH~7.0), thereby removing the unreacted nonsulfated compound. The sulfated homologue was then eluted with a 1M NaCL buffer (pH~7.0), and recovered as a mixture of its trisodium with a NaCl excess. The latter eluate was concentrated, redissolved in a minimum amount of water and passed through a Trisacryl (Gf05 M grade, Sigma-Aldrich) size-exclusion resin column for isolation of the sulfated compound free of NaCl (Scheme 12). Appropriate fractions were pooled and freeze-dried to provide the pure sulfated glycomonomer in 30–35% yield.

n-Pentenyl 2-Acetamido-2-deoxy-3,4,6-trisulfoxy-α-D-glucopyranoside, Trisodium Salt 21(C-3)

$[\alpha]_D^{23}$=+27.8° (c 1.2, $H_2O$). $^1$HNMR ($D_2O$), $\delta_{ppm}$: 1.73 (m, 2H), 2.00 (s, 3H, $NHCOCH_3$), 2.17 (m, 2H), 3.51 (m, 1H), 3.76 (m, 1H), 3.90 (m, 1H), 4.23 (m, 2H), 4.25(m, 1H), 4.59 (m, 2H), 4.90 (d, 1H, J=3.6 Hz, H-1), 5.05 (m, 2H, $CH_2$=), 5.90 (m, 1H, CH=). C NMR ($D_2O$), $\delta_{ppm}$: 24.8, 30.4, 32.4, 55.3, 70.1, 70.4, 71.5, 77.2, 79.4, 99.1, 117.5, 147.7, 177.1. MS/FAB, m/z:595 ($M^+ + 3Na^+ - 3H^+$), 572 ($M^+ + 2Na^+ - 2H^+$).

n-Undecenyl 2-Acetamido-2-deoxy-3,4,6-trisulfoxy-α-D-glucopyranoside, Trisodium Salt, 21(C-9).

$[\alpha]_D^{23}$=+32.0° (c 0.2, $H_2O$). $^1$H NMR ($D_2O$), $\delta_{ppm}$: 1.35 (m, 12H), 1.61 (m, 2H), 2.05 (m, 5H), 3.50 (m, 1H), 3.73 (m, 1H), 3.91 (m, 1H), 4.19 (m, 2H), 4.28 (m, 1H), 4.58 (m, 2H), 4.91 (d, 1H, J=3.7 Hz, H-1), 5.04 (m, 2H, $CH_2$=), 5.91 (m, 1H, CH=). $^{13}C$ NMR ($D_2O$), $\delta_{ppm}$: 24.8, 35.8, 55.3, 70.0, 71.1, 71.2, 79.4, 99.0, 116.7, 143.2, 177.1. MS/FAB, m./z: 679 ($M^+ + 3Na^+ - 3H^+$).

2S-(4,5-disufoxy-6-sulfoxmethyl-3-methylcarboxamidotetrahydro-2H-2-pyranyloxy)ethylacrylate, trisodium salt, 22

$[\alpha]_D^{23}$=−39.0° (c 0.8, $H_2O$). $^1$H NMR ($D_2O$), $\delta_{ppm}$: 1.92 (s, 3H, $CH_3$), 3.34–3.69 (m, 7H), 3.89 (m, 1H), 4.23 (m, 3H), 4.80 (d, 1H, J=3.5 Hz, H-1), 5.82 (d, 1H, J=10.3 Hz, $CH_2$=), 6.07(dd, 1H, J=10.3 and 17.4 Hz, CH=), 6.38 (d, 1H, J=17.4 Hz, $CH_2$=).

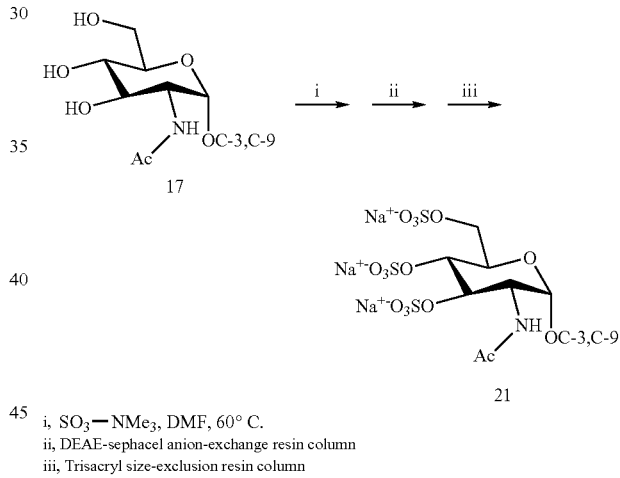

Scheme 12.
Synthesis of Sulfated Alkene-Derivatized Glycomonomers i, $SO_3$—$NMe_3$, DMF, 60° C.
ii, DEAE-sephacel anion-exchange resin column
iii, Trisacryl size-exclusion resin column

Example 18

Statistical Copolymerization of Alkene-Derivatized Glycomonomers and Acrylamide Initiated by $ClC_6H_4N\equiv N^+ BF_4^-/NaOCN$ In a three-neck flask, 6.03×10$^{-5}$ mol (0.008 g) of p-chloroaniline was reacted with 9.04×10$^{-5}$ mol. of $HBF_4$ (actually 0.017 g of 48 wt % aqueous solution), at 0° C., in 2 mL of water and under argon atmosphere. The diazonium salt $ClC_6H_4N\equiv N^+BF_4^-$ was then generated by adding 7.2×10$^{-5}$ mol. (0.005 g) of sodium nitrite ($NaNO_2$) to the reaction medium. After 30 minutes, a degassed mixture of 6.03×10$^{-4}$ mol. (0.225 g) of glycomonomer 17(C-9), 2.41×10$^{-3}$ mol. (0.171 g) of acrylamide, and 6.03×10$^{-5}$ mol. (0.004 g) of sodium cyanate (NaOCN), dissolved in 1 mL of water/tetrahydrofuran (1/1), was introduced into the flask containing the diazonium salt. The polymerization medium was then heated to 50° C. The statistical copolymers formed after 1.5 h and 16 h of reaction were isolated by precipitation in a 10-fold excess of cold methanol, dried and weighed so as to determine the conversion.

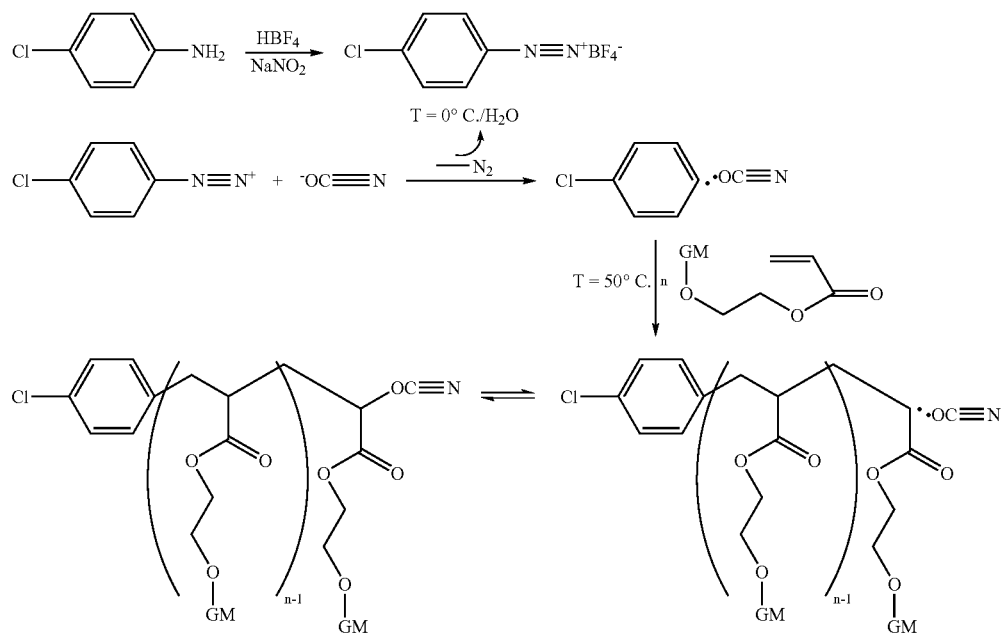

Scheme 13.
Cyanoxyl-Mediated Free-Radical Polymerization of Acrylic Glycomonomers GM = nonsulfated or sulfated N-acetyl-D-glucosamine residue

TABLE 6

Statistical Free-Radical Copolymerization of AM with Alkene-Derivatized Unprotected Glycomonomers Using $ClC_6H_4N{\equiv}N^+BF_4^-$/NaOCN as initiating System[a]

| glycomonomer (GM) | monomer ratio GM/AM (mol) | time (h) | yield[b] (%) | polymer composition[c] GM/AM (mol) | Monosaccharide content (wt %) | $M_n$[d] (g/mol) | $M_w/M_n$ SEC |
|---|---|---|---|---|---|---|---|
| 1 (C-3) | 1/4 | 1.5 | 10 | 1/7 | 38 | 24,100 | 1.46 |
| 1 (C-3) | 1/4 | 16 | 30 | 1/5 | 50 | 43,000 | 1.47 |
| 1 (C-3) | 1/20 | 1.5 | 23 | 1/90 | 04 | 94,000 | 1.17 |
| 1 (C-3) | 1/20 | 16 | 30 | 1/70 | 05 | 112,100 | 1.2 |
| 1 (C-9) | 1/4 | 1.5 | 15 | 1/16 | 25 | 43,400 | 1.25 |
| 1 (C-9) | 1/4 | 16 | 20 | 1/6 | 46 | 99,300 | 1.45 |
| 1 (C-9) | 1/20 | 1.5 | 21 | 1/166 | 03 | 25,800 | 1.14 |
| 1 (C-9) | 1/20 | 16 | 29 | 1/100 | 05 | 28,200 | 1.24 |
| 5 (C-3) | 1/4 | 1.5 | 21 | 1/10 | 44 | 16,100 | 1.13 |
| 5 (C-3) | 1/4 | 16 | 35 | 1/6 | 55 | 57,300 | 1.37 |
| 5 (C-3) | 1/20 | 1.5 | 35 | 1/93 | 07 | 25,400 | 1.10 |
| 5 (C-3) | 1/20 | 16 | 51 | 1/58 | 11 | 47,200 | 1.29 |
| 5 (C-9) | 1/4 | 16 | 26 | 1/10 | 45 | 57,200 | 1.20 |
| 5 (C-9) | 1/20 | 16 | 11 | 1/42 | 17 | 16,300 | 1.17 |

[a]T = 50° C., $[M]_0 = [GM]_0 + [AM]_0 = 1$ mol/L, $[I]_0 = [ClC_6H_4N{\equiv}N^+BF_4^-]_0 = [NaOCN]_0 = 0.02$ mol/L.
[b]Total conversion of comonomers as determined by gravimetry.
[c]Molar ratio of monosaccharide to acrylamide monomeric units in the resulting copolymer as determined by 1H NMR.
[d]$M_n$ obtained from SEC/RI/LLS.

Example 19

Homopolymerization of Acrylic Glycomonomers Initiated by $ClC_6H_4N\equiv N^+BF_4^-/NaOCN$ The general mechanism of this reaction is depicted in Scheme 13, and a typical polymerization is described hereafter. In a three-neck flask, $2.45\times10^{-5}$ mol. (0.003 g) of p-chloroaniline was reacted with $3.67\times10^{-5}$ mol. of $HBF_4$ (actually 0.007 g of 48 wt % aqueous solution), at 0° C., in 2 mL of water and under argon atmosphere. The diazonium salt $ClC_6H_4N\equiv N^+BF_4^-$ was generated by adding $2.93\times10^{-5}$ mol. (0.002 g) of $NaNO_2$ to the reaction medium. After 30 minutes, a degassed mixture of $1.22\times10^{-3}$ mol. (0.39 g) of glycomonomer 19 and $2.45\times10^{-5}$ mol. (0.002 g) of NaOCN, dissolved in 0.5 mL of water, was introduced into the flask containing the arenediazonium salt. The polymerization medium was then heated to 50° C. for 4 h. The resulting glycopolymer was isolated by precipitation in a 10-fold excess of cold methanol and dried to yield a white cotton wool-like material.

TABLE 7

Free-Radical Homopolymerization of Acrylic Unprotected Glycomonomers and Statistical Copolymerization with AM Using $ClC_6H_4N\equiv N^+BF_4^-/NaOCN$ as Initiating System

| glycomonomer (GM) | monomer ratio GM/AM (mol) | time (h) | yield[e] (%) | polymer composition[f] GM/AM (mol) | monosaccharide content (wt %) | $M_n$[g] (g/mol) | $M_w/M_n$ SEC |
|---|---|---|---|---|---|---|---|
| 3[a] | 1/0 | 4 | 25 | 1/0 | 100 | 15,400 | 1.26 |
| 3[b] | 1/0 | 1.5 | 40 | 1/0 | 100 | 77,100 | 1.45 |
| 3[b] | 1/0 | 4 | 70 | 1/0 | 100 | 127,000 | 1.56 |
| 3[b] | 1/1 | 1.5 | 88 | 1/1.5 | 75 | 47,400 | 1.57 |
| 3[b] | 1/4 | 1.5 | 33 | 1/7 | 40 | 30,600 | 1.35 |
| 3[b] | 1/4 | 4 | 93 | 1/6 | 43 | 51,700 | 1.55 |
| 6[c] | 1/0 | 4 | 35 | 1/0 | 100 | 9,900 | 1.13 |
| 6[d] | 1/0 | 4 | 25 | 1/0 | 100 | 20,800 | 1.49 |
| 6[c] | 1/1 | 1.5 | 20 | 1/4 | 66 | 48,000 | 1.45 |
| 6[c] | 1/1 | 4 | 25 | 1/2 | 80 | 59,500 | 1.47 |
| 6[c] | 1/4 | 1.5 | 95 | 1/9 | 42 | 115,600 | 1.57 |

[a]T = 50° C., $[M]_0 = [GM]_0 + [AM]_0 = 1$ mol/L, $[I]_0 = [ClC_6H_4N\equiv N^+BF_4^-]_0 = [NaOCN]_0 = 0.1$ mol/L.
[b]T = 50° C., $[M]_0 = 1$ mol/L, $[I]_0 = 0.02$ mol/L.
[c]T = 50° C., $[M]_0 = 0.5$ mol/L, $[I]_0 = 0.05$ mol/L.
[d]T = 50° C., $[M]_0 = 0.05$ mol/L, $[I]_0 = 0.01$ mol/L.
[e]Total conversion of comonomers as determined by gravimetry.
[f]Molar ratio of monosaccharide to acrylamide monomeric units in the resulting copolymer as determined by 1H NMR.
[g]$M_n$ obtained from SEC/RI/LLS.

This invention has been illustrated using specific examples of linking groups, saccharides, second units, and reagents. However, as will be apparent to those skilled in the art, other equivalent components and reagents can be substituted for those specifically mentioned herein. Such equivalents are included within the scope of the following claims.

The invention claimed is:

1. A glycopolymer composition comprising glycopolymer molecules having:
   a polymer backbone comprising a straight chain or branched hydrocarbon;
   a first pendent unit connected to said polymer backbone comprising:
   a linking group;
   a saccharide moiety connected to said linking group;
   an optional second pendent unit connected to said polymer backbone wherein said second pendent unit comprises a hydrocarbyl monomer;
   a phenyl ring at a first end of said polymer backbone; and
   a cyanoxyl group at a second end of said polymer backbone.

2. The glycopolymer composition of claim 1 wherein said linking group comprises about 3 to about 9 carbon atoms.

3. The glycopolymer composition of claim 1 having a polydispersity index between about 1.1 and about 1.5.

4. The glycopolymer composition of claim 1 wherein said polymer backbone is branched.

5. The glycopolymer composition of claim 1 wherein said saccharide moiety is selected from the group consisting of monosaccharides, disaccharides, trisaccharides and oligosaccharides.

6. The glycopolymer composition of claim 1 wherein said saccharide moiety comprises N-acetyl-D-glucosamine.

7. The glycopolymer composition of claim 1 wherein said saccharide moiety comprises α-N-acetyl-D-glucosamine-(1→4)-D-glucuronic acid or β-N-acetyl-D-glucosamine-(1→4)-D-glucuronic acid.

8. The glycopolymer composition of claim 1 wherein said saccharide moiety comprises pyranosides.

9. The glycopolymer composition of claim 1 wherein said saccharide moiety comprises lactose.

10. The glycopolymer composition of claim 1 wherein said saccharide moiety is fully or partially sulfated.

11. The glycopolymer composition of claim 1 comprising at least one additional first pendent unit; wherein said first pendent units are situated in trans-configuration along said polymer backbone.

12. The glycopolymer composition of claim 1 comprising at least one additional first pendent unit; wherein said first pendent units are situated in cis-configuration along said polymer backbone.

13. The glycopolymer composition of claim 1 wherein said second pendent unit is produced by copolymerization with a monomer selected from the group consisting of acrylamide, acrylate, or alkenyl compounds.

14. The glycopolymer composition of claim 13 wherein said monomer is acrylamide.

15. The glycopolymer composition of claim 13 wherein said monomer is an alkenyl compound.

16. The glycopolymer composition of claim 1 comprising at least one additional first pendent unit; wherein the number of said first pendent units is between about 2 and about 1000.

17. The glycopolymer composition of claim 1 comprising at least one additional first pendent unit and at least one additional second pendent unit; wherein the total number of said first pendent units and second pendent units is no more than about 200.

18. The glycopolymer composition of claim 1 comprising at least one additional first pendent unit and at least one additional second pendent unit; wherein the sum of said first pendent units and said second pendent units is no more than about 1000.

19. The glycopolymer composition of claim 1 comprising at least one additional second pendent unit; wherein said molecules comprise up to about 1000 of said second pendent units.

20. The glycopolymer composition of claim 1 comprising at least one additional first pendent unit and at least one additional second pendent unit; wherein said first pendent units and said second pendent units are interspersed with each other in random order.

21. The glycopolymer composition of claim 1 wherein said phenyl ring is chlorophenyl.

22. The glycopolymer composition of claim 1 wherein said ring comprises a para substituent.

23. The glycopolymer composition of claim 22 wherein said substituent is selected from the group consisting of optionally substituted hydrocarbyl, alcohol, amine, polyamine, sulfate, phosphate, and halogen; wherein halogen is selected from the group consisting of chlorine, bromine and iodine; and salts of the foregoing.

24. The glycopolymer composition of claim 1 bound to cytokine or growth factor molecules.

25. The glycopolymer composition of claim 1 wherein said molecules comprise hydrophilic moieties capable of rendering said composition water-soluble.

26. The glycopolymer composition of claim 1 wherein said molecules have the general formula:

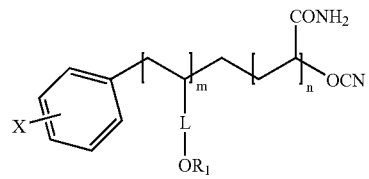

wherein $X=H$, Cl, $NO_2$ or $OCH_3$; L is a linker selected from the group consisting of —$(CH_2)_p$— with p between 3 and about 9, and —$COO(CH_2)_2$—; $OR_1$ is selected from the group consisting of saccharide moieties; m is between 2 and about 1000; n is between 0 and about 1000; and wherein individual portions designated by m and n may be in any order.

27. A method of making a cyanoxyl-glycopolymer comprising comprising:
 a) providing a cyanoxyl radical of an arenediazonium salt;
 b) providing glycomonomers comprising terminal vinyl groups;
 c) polymerizing said glycomonomers in the presence of said cyanoxyl radicals.

28. The method of claim 27 also providing acrylamide molecules comprising terminal vinyl groups.

29. The method of claim 28 comprising providing said glycomonomers and acrylamide molecules at a ratio of about 1:4 glycomonomer:acrylamide.

30. The method of claim 27 wherein said glycomonomers are fully or partially sulfated.

31. The method of claim 27 wherein said glycomonomers are made by attaching at least one saccharide residue to an alkenyl, acrylate or acylamide linkage.

32. The method of claim 27 wherein said cyanoxyl radical is made by contacting an arenediazonium salt with a cyanate anion.

33. The method of claim 27 performed at a temperature between about 50 and about 70 degrees C.

* * * * *